United States Patent
Singh et al.

(10) Patent No.: US 12,343,176 B2
(45) Date of Patent: Jul. 1, 2025

(54) SENSOR SIGNAL PROCESSING WITH KALMAN-BASED CALIBRATION

(71) Applicant: KONAMITE LIMITED, Dublin (IE)

(72) Inventors: Abhinoy Kumar Singh, Indore (IN); Mihailo V. Rebec, Portland, OR (US); Ahmad Haidar, Montreal (CA)

(73) Assignee: Konamite Limited, Dublin (IE)

( * ) Notice: Subject to any disclaimer, the term of this patent is extended or adjusted under 35 U.S.C. 154(b) by 385 days.

(21) Appl. No.: 17/956,642

(22) Filed: Sep. 29, 2022

(65) Prior Publication Data

US 2023/0034606 A1 Feb. 2, 2023

Related U.S. Application Data

(63) Continuation of application No. 16/893,084, filed on Jun. 4, 2020, now abandoned.
(Continued)

(51) Int. Cl.
*A61B 5/00* (2006.01)
*A61B 5/145* (2006.01)
(Continued)

(52) U.S. Cl.
CPC .......... *A61B 5/725* (2013.01); *A61B 5/14532* (2013.01); *A61B 5/7278* (2013.01);
(Continued)

(58) Field of Classification Search
None
See application file for complete search history.

(56) References Cited

U.S. PATENT DOCUMENTS

| | | | |
|---|---|---|---|
| 7,436,511 B2 | 10/2008 | Ruchti | |
| 9,662,056 B2 | 5/2017 | Budiman | |

(Continued)

FOREIGN PATENT DOCUMENTS

| | | |
|---|---|---|
| AU | 754677 B2 | 11/2002 |
| CN | 102740770 | 10/2012 |

(Continued)

OTHER PUBLICATIONS

Patent Cooperation Treaty: International Search Report and Written Opinion for PCT/US2020/036124 dated Aug. 20, 2020; 10 pages.
(Continued)

*Primary Examiner* — Michael R Bloch
(74) *Attorney, Agent, or Firm* — Fish & Richardson P.C.

(57) ABSTRACT

Methods, systems, and computer readable media are disclosed for estimating an amount of an analyte in blood of a subject. In an example, a method includes obtaining a noise filtered current by noise filtering a current received from an analyte sensor placed interstitially in tissue of the subject, estimating one or more blood analyte calibration parameters based on the noise filtered current, obtaining a second set of one or more interstitial analyte calibration parameters based at least in part on the one or more blood analyte calibration parameters, and estimating the amount of the analyte in the blood of the subject based on the noise filtered current and the one or more interstitial analyte calibration parameters. In this way, an analyte sensor that is placed interstitially may readily be calibrated to report accurate blood analyte values.

20 Claims, 9 Drawing Sheets

Related U.S. Application Data

(60) Provisional application No. 62/857,242, filed on Jun. 4, 2019.

(51) Int. Cl.
*A61M 5/172* (2006.01)
*G16H 50/00* (2018.01)

(52) U.S. Cl.
CPC .......... *A61M 5/1723* (2013.01); *G16H 50/00* (2018.01); *A61B 5/742* (2013.01)

(56) References Cited

U.S. PATENT DOCUMENTS

| | | | |
|---|---|---|---|
| 2008/0033254 A1* | 2/2008 | Kamath | A61B 5/725 600/300 |
| 2011/0184267 A1* | 7/2011 | Duke | A61B 5/725 600/365 |
| 2011/0237917 A1* | 9/2011 | Roy | A61B 5/1495 702/19 |
| 2013/0109944 A1* | 5/2013 | Sparacino | A61B 5/746 600/365 |
| 2013/0245401 A1 | 9/2013 | Estes et al. | |
| 2016/0029966 A1 | 2/2016 | Salas-Boni et al. | |
| 2016/0287184 A1 | 10/2016 | Diebold | |
| 2016/0354543 A1* | 12/2016 | Cinar | G16H 40/63 |
| 2017/0049964 A1* | 2/2017 | Varsavsky | G16H 40/40 |
| 2017/0181677 A1 | 6/2017 | Varsavsky et al. | |
| 2017/0272842 A1* | 9/2017 | Touma | A63B 24/0003 |
| 2020/0383643 A1 | 12/2020 | Singh | |

FOREIGN PATENT DOCUMENTS

| | | |
|---|---|---|
| CN | 102821687 | 12/2012 |
| CN | 107949883 | 4/2018 |
| WO | 2011/119201 A2 | 9/2011 |
| WO | 2016/054046 A1 | 4/2016 |
| WO | 2020/247632 A1 | 12/2020 |

OTHER PUBLICATIONS

Rousseux et al., "Deconvolution of Time-barring Systems by Kalman Filtering: Its Application to the Computation of the Active State in the Muscle," Signal Processing 10 (1986) 291-301.

Extended European Search Report in European Appln. No. 20796466.9, mailed on Jan. 26, 2022, 7 pages.

International Preliminary Report on Patentability in International Appln. No. PCT/US2020/036124, mailed on Dec. 16, 2021, 9 pages.

Wikipedia.com [online], "Moving average," Nov. 23, 2024, retrieved Jan. 2, 2025, retrieved from URL <https://en.wikipedia.org/wiki/Moving_average>, 8 pages.

* cited by examiner

SENSOR SIGNAL PROCESSING WITH KALMAN-BASED CALIBRATION

CROSS-REFERENCE TO RELATED APPLICATION

This application is a continuation of U.S. patent application Ser. No. 16/893,084, filed Jun. 4, 2020 which in turn claims the benefit of U.S. Provisional Application No. 62/857,242, filed Jun. 4, 2019, both of which are titled "Sensor Signal Processing With Kalman-Based Calibration" and both of which are incorporated herein by reference in their entirety.

TECHNICAL FIELD

Embodiments herein relate to the field of continuous analyte monitoring, and, more specifically, to the calibration of a continuous analyte monitoring system to obtain consistent readings and reduce background artifacts.

BACKGROUND

Blood glucose levels are mainly regulated by a hormone called insulin, secreted from the pancreatic β-cells. In type 1 diabetes, insulin secretion is lost due to an autoimmune process that destroys the β-cells. Type 1 diabetes can be treated in some examples with life-long insulin replacement therapy that aims at maintaining glucose levels in a tight target range in order to avoid long-term macro- and micro-vascular complications. However, delivering the right amount of insulin can be challenging, due at least in part to the intermittent nature of traditional glucose meters (4-7 measurements per day). For example, glucose levels may often undergo large swings in short periods of time. Such fluctuations may be undetected, resulting in unrecognized hypoglycemia (low glucose levels) and hyperglycemia (high glucose levels) events. To overcome these issues, continuous glucose monitoring systems have been developed to measure glucose levels at much shorter predetermined intervals (e.g., every 5 minutes or less). Use of such continuous glucose monitoring (CGM) systems can improve one's ability to control glucose levels. In some examples, such CGM systems may be combined with insulin pumps for closed-loop control of insulin delivery. Examples where a CGM system is combined with an insulin pump that receives instructions based on glucose levels monitored by the CGM system may be referred to as artificial pancreas systems.

A continuous glucose monitoring system may include a glucose sensor that is implanted under the skin, and which may generate an electrical current proportional to interstitial glucose levels. The sensitivity of such a sensor can vary between individuals, as well as with sensor wear time. Thus, sensor calibration is an important aspect of any glucose monitoring system. Calibration methodology may attempt to account for one or more of intra- and inter-individual variability in sensor sensitivity, measurement noise, and a difference between the interstitial and blood (or capillary) compartments. A glucose sensor that is not properly calibrated may result in the reporting of erroneous glucose levels, which may degrade an ability to manage a disease condition related to glucose control.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF THE DISCLOSURE

Figure 1:
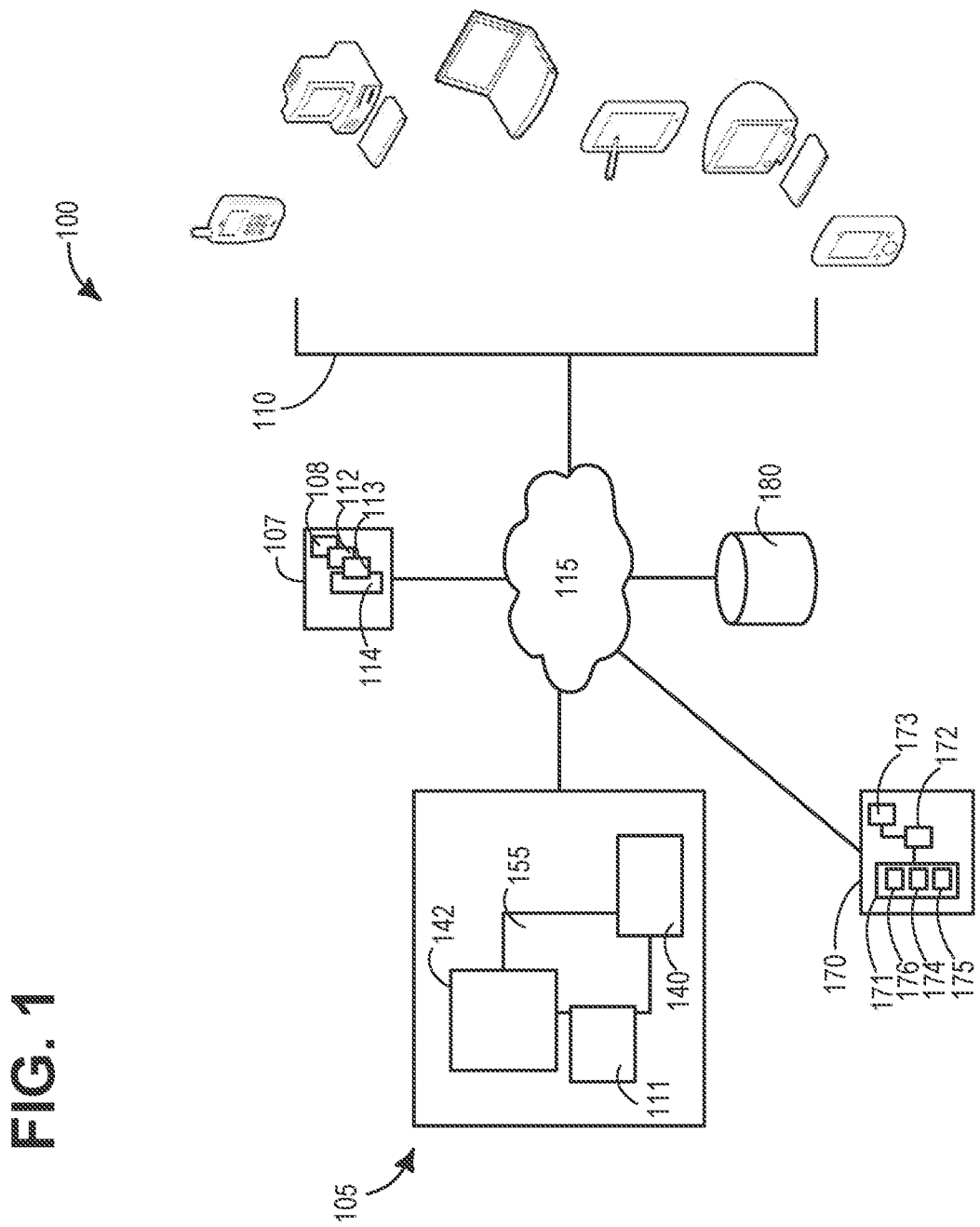
FIG. 1 depicts an example continuous analyte monitoring (CAM) system, including an analyte sensor computing apparatus for calibration of an analyte sensor, in accordance with embodiments herein.

In the following detailed description, reference is made to the accompanying drawings which form a part hereof, and in which are shown by way of illustration embodiments that may be practiced. It is to be understood that other embodiments may be utilized, and structural or logical changes may be made without departing from the scope. Therefore, the following detailed description is not to be taken in a limiting sense, and the scope is defined by the appended claims and their equivalents.

Various operations may be described as multiple discrete operations in turn, in a manner that may clarify the disclosure; however, the order of description should not be construed to imply that these operations are order dependent.

The description may use perspective-based descriptions such as up/down, back/front, and top/bottom. Such descriptions are merely used to facilitate the discussion and are not intended to restrict the scope of the disclosure.

The terms "coupled" and "connected," along with their derivatives, may be used. These terms are not intended as synonyms for each other. Rather, aspects, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Continuous glucose monitoring technology has been used in the management of diabetes for some time. As one example, glucose monitoring devices may utilize enzymatic methods to measure glucose concentration and provide sample information. In some applications, the continuous glucose sensor may comprise a component of a closed loop insulin delivery system and, as such, should be selective, rapid, predictable and acceptable for continuous patient use.

A number of calibration methods have been reported, yet there are various drawbacks to each and hence room for further development. For example, some analyte sensor calibration methodologies assume a constant current-to-analyte relationship between calibration times, which may not be the case. Other drawbacks associated with other calibration methodologies include but are not limited to the use of device-specific functions and the use of priors that are based on offline historical population-level data rather than patient-specific previous data.

The inventors herein have recognized the above-mentioned issues, and have developed approaches to at least partially address them. In one example, a method of estimating an amount of an analyte in blood of a subject comprises receiving, from an analyte sensor placed in interstitial fluid of the subject, a current reflective of an interstitial level of the analyte. The method further includes noise filtering the current to provide a noise filtered current. A first set of one or more blood analyte calibration parameters is estimated based at least in part on the noise filtered current. A second set of one or more interstitial analyte calibration parameters is obtained based at least in part on the first set of one or more blood analyte calibration parameters. The amount of the analyte in the blood of the subject is estimated based on the second set of one or more interstitial analyte calibration parameters and the noise filtered current.

In an example, noise filtering the current values further comprises filtering out both a low frequency high magnitude noise component and a high frequency low magnitude component. The low frequency high magnitude noise component is filtered heuristically and the high frequency low magnitude component is filtered via Kalman filtering.

In another example of the method, estimating the first set of one or more blood analyte calibration parameters further comprises deconvoluting the noise filtered current via a sequential Kalman filter to obtain a hypothetical analyte sensor current assuming the analyte sensor is inserted in the blood instead of the interstitial fluid. The first set of one or more blood glucose calibration parameters is estimated based on the hypothetical analyte sensor current using a Kalman filter that uses the hypothetical analyte sensor current as a measurement variable. The method further includes obtaining a capillary blood analyte measurement, where estimating the first set of one or more blood analyte calibration parameters is based on the capillary blood glucose measurement.

In another example of the method, the method further comprises determining an initial blood analyte calibration parameter state estimate, and a blood analyte calibration parameter covariance, for initialization of the sequential Kalman filter. The initial blood analyte calibration parameter state estimate and the blood analyte calibration parameter covariance may be determined using a nonlinear Kalman filter. As an example, the nonlinear Kalman filter is a cubature Kalman filter. For such a method, determining the initial blood analyte calibration parameter state estimate and the blood analyte calibration parameter covariance may be based on one or more training data sets. In another additional or alternative example, the method may include determining the initial blood analyte calibration parameter state estimate and the blood analyte calibration parameter covariance arbitrarily. In another additional or alternative example, determining the initial blood analyte calibration parameter state estimate and the blood analyte calibration parameter covariance may be based on one or more prior analyte sensor calibration events.

In a representative example of the method, the analyte sensor is a glucose sensor, and the analyte is glucose. In such an example, an embodiment includes sending one or more instructions to an insulin delivery system for controlling operation of an insulin pump that in turn delivers an appropriate amount of insulin to the subject, where the one or more instructions are based on the estimated amount of analyte in the blood of the subject. Additionally, or alternatively, the method may further comprise displaying the estimated amount of glucose in the blood of the subject on a display screen associated with the glucose sensor, for viewing by the subject.

In another aspect, a system for estimating an amount of an analyte in a subject comprises an analyte sensor, and a mobile computing device. The mobile computing device includes a processor storing instructions in non-transitory memory that, when executed, cause the processor to receive from the analyte sensor a current reflective of an interstitial level of the analyte in the subject, noise filter the current to obtain a noise filtered current, and estimate one or more blood analyte calibration parameters based on the noise filtered current. Based on the one or more blood analyte calibration parameters, the instructions further cause the processor to obtain one or more interstitial analyte calibration parameters, and estimate the amount of the analyte in the blood of the subject based on the one or more interstitial analyte calibration parameters and the noise filtered current.

In an example of the system, the processor stores further instructions in non-transitory memory that, when executed, cause the processor to obtain the noise filtered current by heuristically filtering out a low frequency high magnitude noise component of the current, and by Kalman-based filtering of a high frequency low magnitude noise component of the current.

In another example of the system, the processor stores further instructions in non-transitory memory that, when executed, cause the processor to deconvolute the noise filtered current via a sequential Kalman filter to obtain a predicted blood analyte sensor current. The instructions, when executed, further cause the processor to estimate the one or more blood glucose calibration parameters based on the predicted blood analyte sensor current via a Kalman filter that uses the predicted analyte sensor current as a measurement variable. In some examples, the processor stores further instructions that, when executed, cause the processor to estimate the one or more blood glucose calibration parameters based on a capillary blood glucose measurement.

In some examples of the system, the processor stores further instructions that, when executed, cause the processor to determine an initial blood analyte calibration parameter state estimate, and an initial blood analyte calibration parameter covariance, and initialize the sequential Kalman filter based on the initial blood analyte calibration parameter state estimate and the initial blood analyte calibration parameter covariance. In an embodiment, the initial blood analyte calibration parameter state estimate, and the initial blood analyte calibration parameter covariance are determined via a nonlinear Kalman filter. In some examples, the nonlinear filter may be a cubature Kalman filter. In an example, the initial blood analyte calibration parameter state estimate, and the initial blood analyte calibration parameter covariance, are arbitrarily assigned. In another additional or alternative example, the initial blood analyte calibration parameter state estimate, and the initial blood analyte calibration parameter covariance are determined based on one or more prior analyte sensor calibration events. In another additional or alternative example, the initial blood analyte calibration parameter state estimate, and the initial blood analyte calibration parameter covariance are determined based on one or more training data sets.

In another example of the system, the analyte sensor is a glucose sensor and the analyte is glucose. In such an example, the system may further comprise an insulin delivery unit that includes at least an insulin pump and an infusion set. The processor in such an example may store further instructions that, when executed, cause the processor to determine an insulin injection amount for the subject based on the estimated amount of the analyte in the blood of the subject, and send one or more instructions to the insulin delivery unit to control the insulin pump to deliver the insulin injection amount to the subject via the infusion set. In another additional or alternative example, the mobile computing device may further comprise a display. In such an example, the processor may store further instructions that, when executed, cause the processor to provide the amount of the analyte in the blood of the subject in a viewable form on the display, for viewing by the subject.

In yet another aspect, disclosed is a non-transitory computer-readable storage medium with an executable program stored thereon for calibrating an analyte sensor inserted into the tissue of a subject. The program instructs a microprocessor to perform the steps of receiving from the analyte sensor a current reflective of an interstitial amount of an analyte in the subject, noise filtering the current received from the analyte sensor to provide a noise filtered current, estimating a first set of one or more blood analyte calibration parameters based on the noise filtered current, obtaining a second set of one or more interstitial analyte calibration parameters based on the first set of one or more blood analyte calibration parameters, and estimating an amount of the analyte in the blood of the subject based on the second set of one or more interstitial analyte calibration parameters and the noise filtered current.

In an example of the computer-readable storage medium, the program further instructs the microprocessor to filter out low frequency high magnitude noise heuristically and filter out high frequency low magnitude noise via Kalman filtering.

In another example of the computer-readable storage medium, the program further instructs the microprocessor to estimate the first set of one or more blood analyte calibration parameters by deconvoluting the noise filtered current via a sequential Kalman filter to obtain a predicted blood analyte sensor current that accounts for interstitial-to-blood analyte diffusion dynamics. The program further instructs the microprocessor to estimate the first set of one or more blood analyte calibration parameters based on the predicted blood analyte sensor current via a Kalman filter that uses the hypothetical analyte sensor current as a measurement variable. In an embodiment, the program further instructs the microprocessor to estimate the first set of one or more blood analyte calibration parameters based at least in part on one or more capillary blood analyte measurements.

In an example of the computer-readable storage medium, the program further instructs the microprocessor to determine an initial blood analyte calibration parameter state estimate, and an initial blood analyte calibration parameter covariance, for initiation of the sequential Kalman filter. In an example, the initial blood analyte calibration parameter state estimate, and the initial blood analyte calibration parameter covariance, are determined via a nonlinear Kalman filter. The nonlinear Kalman filter may comprise a cubature Kalman filter, in an example.

In an example of the non-transitory computer-readable storage medium, the program further instructs the microprocessor to determining the initial blood analyte calibration parameter state estimate and the blood analyte parameter covariance based on one or more training data sets. In another additional or alternative example, the program instructs the microprocessor to arbitrarily determine the initial blood analyte calibration parameter state estimate and the blood analyte parameter covariance. In another additional or alternative example, the program further instructs the microprocessor to determine the initial blood analyte calibration parameter state estimate and the blood analyte parameter covariance based on one or more prior analyte sensor calibration events.

In a representative example of the non-transitory computer-readable storage medium, the analyte sensor is a glucose sensor, and the analyte is glucose. In such an example, the program may further instruct the microprocessor to determine an insulin injection amount for the subject based on the estimated amount of the analyte in the blood of the subject, and provide one or more instructions pertaining to controlling an insulin pump based on the insulin injection amount, the instructions for use via the insulin pump. In another additional or alternative example, the program may further instruct the microprocessor to provide one or more instructions for displaying the estimated amount of the analyte in the blood of the subject on a display viewable by the subject.

Accordingly, as a representative example, disclosed herein is a glucose estimation method that uses Kalman filtering to estimate parameters of an analyte sensor model. The model uses an affine function to describe time-varying sensitivity. To account for interstitial-to-blood dynamics, a noise-filtered current signal from the analyte sensor is deconvoluted using a sequential Kalman filter, and the deconvoluted signal is then used to obtain blood analyte calibration parameters and in turn, interstitial analyte calibration parameters. The interstitial analyte calibration parameters are then used in conjunction with the noise-filtered current signal to estimate blood glucose level, for example blood glucose concentration. At calibration times, the most recent calibration parameters may serve as priors, which implicitly include information from all previous days and previous capillary glucose measurements. For day 1 (the day at which the analyte sensor is inserted into tissue of a subject), the calibration parameters may be obtained using a computationally-efficient nonlinear cubature Kalman filter applied to historical datasets. As disclosed herein, the performance of the method was applied by testing on twenty sensor datasets collected in real patients over a 7-day period.

Turning to FIG. 1, disclosed herein is an example networked continuous analyte monitoring (CAM) system 100, in accordance with embodiments herein. In examples where the CAM system 100 is used to monitor glucose levels in a subject over time, the CAM system may be referred to as continuous glucose monitoring (CGM) system 100.

The networked CAM system 100 includes an analyte sensor computing device 105 in wired or wireless communication with one or more analyte sensing devices 107 via network 115. Discussed herein, the one or more analyte sensing device(s) 107 may also be referred to as analyte sensor(s), or simply, sensors. In examples where the analyte sensor(s) comprise glucose sensors, the analyte sensor(s) may be referred to as CGM sensor(s), glucose sensors, or simply, sensors. The networked CAM system 100 may also include other networked devices 110 (e.g., laptop, desktop computer, tablet, smartphone, servers, mass storage devices, etc.), which may be in wired or wireless communication with analyte sensor computing device 105 and/or the one or more analyte sensor(s) 107 via network 115. In some embodiments, the analyte sensor computing device 105 includes application software with executable instructions configured to transmit and receive information from network 115. The information can be transmitted to and/or received from another device, such as one or more networked devices 110 through network 115. In certain examples, the analyte sensor computing device 105 may also be capable of transmitting information about analyte measurements retrieved from one or more of analyte sensor(s) 107 of a subject to one or more of a doctor, other medical practitioner, and insulin delivery system 170.

As depicted at FIG. 1, the CAM system 100 distributes and receives information to and from one or more networked devices (e.g., analyte sensor computing device 105, networked devices 110) through one or more of network 115. According to various embodiments, network 115 may be any network that allows computers to exchange data, for example for cloud based storage of data generated (historical and current) and/or implementation of some, none, or even all of the methods disclosed herein. Depicted at FIG. 1 is database 180, which in some examples may comprise cloud-based data storage. In some embodiments, network 115 includes one or more network elements (not shown) capable of physically or logically connecting computers. The network 115 may include any appropriate network, including an intranet, the Internet, a cellular network, a local area network (LAN), a wide area network (WAN), a personal network or any other such network or combination thereof. Components used for such a system can depend at least in part upon the type of network and/or environment selected. Protocols and components for communicating via such a network are well known and will not be discussed herein in detail. In embodiments, communication over the network 115 are enabled by wired or wireless connections, and combinations thereof. Network 115 includes a wired or wireless telecommunication means by which network systems may communicate and exchange data. For example, network 115 is implemented as, or may be a part of, a storage area network (SAN), personal area network (PAN), a metropolitan area network (MAN), a local area network (LAN), a wide area network (WAN), a wireless local area network (WLAN), a virtual private network (VPN), an intranet, an Internet, a mobile telephone network, such as Global System for Mobile Communications (GSM), General Packet Radio Service (GPRS), CDMAOne, CDMA2000, Evolution-Data Optimized (EV-DO), Enhanced Data Rates for GSM Evolution (EDGE), Universal Mobile Telecommunications System (UMTS), Digital Enhanced Cordless Telecommunications (DECT), Digital AMPS (IS-136/TDMA), and Integrated Digital Enhanced Network (iDEN), Long-Term Evolution (LTE), $3^{rd}$ generation mobile network (3G), 4th generation mobile network (4G), and/or 5th generation mobile network (5G) networks, a card network, Bluetooth, near field communication network (NFC), any form of standardized radio frequency, or any combination thereof, or any other appropriate architecture or system that facilitates the communication of signals, data, and/or messages (generally referred to as data). Throughout this specification, it should be understood that the terms "data" and "information" are used interchangeably herein to refer to text, images, audio, video, or any other form of information that can exist in a computer-based environment.

In an example embodiment, each of analyte sensor computing device 105 and networked devices 110 may comprise a device having a communication component capable of transmitting and/or receiving data over network 115. For example, each networked device 110 may comprise a server, personal computer, mobile device (for example, notebook computer, tablet computer, netbook computer, personal digital assistant (PDA), video game device, GPS locator device, cellular telephone, smartphone, or other mobile device), a television with one or more processors embedded therein and/or coupled thereto, or other appropriate technology that includes or is coupled to a web browser or other application for communicating via the network 115.

Analyte sensor computing device 105 may be any computing device, such as a smart phone, tablet, desktop computer, laptop, or even a standalone chip included as part of the analyte sensor 107, etc., for crossover-calibrating a sensor (e.g., analyte sensor(s) 107 at FIG. 1) inserted into the tissue of a subject, in accordance with embodiments herein. In embodiments, analyte sensor computing device 105 includes several components, such as one or more processors 140 and at least one sensor communication module 142, for example that is capable of communication with a sensor (e.g., analyte sensor(s) 107 at FIG. 1). In various embodiments, the one or more processors 140 each include one or more processor cores. In various embodiments, the at least one sensor communication module 142 is physically and electrically coupled to the one or more processors 140. In various embodiments, the at least one sensor communication module 142 is physically and/or electrically coupled to the one or more sensors, such as analyte sensor 107. In some examples, it may be understood that the analyte sensor computing device 105 and the analyte sensor 107 may comprise a single device, without departing from the scope of this disclosure.

In further implementations, the sensor communication module 142 is part of the one or more processors 140. In various embodiments, analyte sensor computing device 105 includes printed circuit board (PCB) 155. For these embodiments, the one or more processors 140 and sensor communication module 142 is disposed thereon. Depending on its applications, the analyte sensor computing device 105 includes other components that may or may not be physically and electrically coupled to the PCB. These other components include, but are not limited to, a memory controller (not shown), volatile memory (e.g., dynamic random access memory (DRAM) (not shown)), non-volatile memory (not shown) such as read only memory (ROM), flash memory (not shown), an I/O port (not shown), (not shown), a digital signal processor (not shown), a crypto processor (not shown), a graphics processor (not shown), one or more antenna (not shown), a touch-screen display 111, a touch-screen display controller (not shown), a battery (not shown), an audio codec (not shown), a video codec (not shown), a global positioning system (GPS) device (not shown), a compass (not shown), an accelerometer (not shown), a temperature monitor, a gyroscope (not shown) (not shown), a speaker (not shown), a camera (not shown), and a mass storage device (such as hard disk drive, a solid state drive, compact disk (CD) (not shown), digital versatile disk (DVD) (not shown), a microphone (not shown), and so forth.

In some embodiments, the one or more processors 140 is/are operatively coupled to system memory through one or more links (e.g., interconnects, buses, etc.). In embodiments, system memory is capable of storing information that the one or more processors 140 utilizes to operate and execute programs and operating systems, including computer readable instructions for the method disclosed herein. In different embodiments, system memory is any usable type of readable and writeable memory such as a form of dynamic random access memory (DRAM). In embodiments, analyte sensor computing device 105 includes or is otherwise associated with various input and output/feedback devices to enable user interaction with the analyte sensor computing device 105 and/or peripheral components or devices associated with the analyte sensor computing device 105 by way of one or more user interfaces or peripheral component interfaces. In embodiments, the user interfaces include, but are not limited to a physical keyboard or keypad, a touchpad, a display device (touchscreen or non-touchscreen), speakers, microphones, sensors, such as glucose sensors, haptic feedback devices and/or one or more actuators, and the like.

In some embodiments, the analyte sensor computing device 105 can comprise a memory element (not shown), which can exist within a removable smart chip or a secure digital ("SD") card or which can be embedded within a fixed chip. In certain example embodiments, Subscriber Identity Component ("SIM") cards may be used. In various embodiments, the memory element may allow a software application resident on the device.

In embodiments, an I/O link connecting a peripheral device to the analyte sensor computing device 105 is protocol-specific with a protocol-specific connector port that allows a compatible peripheral device to be attached to the protocol-specific connector port (i.e., a USB keyboard device would be plugged into a USB port, a router device would be plugged into a LAN/Ethernet port, etc.) with a protocol-specific cable. Any single connector port would be limited to peripheral devices with a compatible plug and compatible protocol. Once a compatible peripheral device is plugged into the connector port, a communication link would be established between the peripheral device and a protocol-specific controller.

In embodiments, a non-protocol-specific connector port is configured to couple the I/O interconnect with a connector port of the analyte sensor computing device 105, allowing multiple device types to attach to the analyte sensor computing device 105 through a single physical connector port. Moreover, the I/O link between the analyte sensor computing device 105 and the I/O complex is configured to carry multiple I/O protocols (e.g., PCI Express®, USB, DisplayPort, HDMI, etc.) simultaneously. In various embodiments, the connector port is capable of providing the full bandwidth of the link in both directions with no sharing of bandwidth between ports or between upstream and downstream directions. In various embodiments, the connection between the I/O interconnect and the analyte sensor computing device 105 supports electrical connections, optical connections, or both.

In some embodiments, the one or more processors 140, flash memory, and/or a storage device includes associated firmware storing programming instructions configured to enable the analyte sensor computing device 105, in response to execution of the programming instructions by one or more processors 140, to practice all or selected aspects of a method of calibrating a sensor (e.g., analyte sensor(s) 107 at FIG. 1) inserted into the tissue of a subject using a computing device, in accordance with embodiments of the present disclosure.

In embodiments, the sensor communication module 142 may enable wired and/or wireless communications for the transfer of data to and from the analyte sensor computing device 105, for example to and/or from one or more sensors, (e.g., analyte sensor(s) 107 at FIG. 1). As one example, sensor communication module 142 may comprise a transmitter and/or a transmitter/receiver. In some examples, the transmitter and/or transmitter/receiver may be coupled, for example physically and/or electrically, to one or more sensors (e.g., analyte sensor(s) 107 at FIG. 1).

In various embodiments, the analyte sensor computing device 105 also includes a network interface configured to connect the analyte sensor computing device 105 to one or more networked computing devices wirelessly via a transmitter and a receiver (or optionally a transceiver) and/or via a wired connection using a communications port. In embodiments, the network interface and the transmitter/receiver and/or communications port are collectively referred to as a "communication module". In embodiments, the wireless transmitter/receiver and/or transceiver may be configured to operate in accordance with one or more wireless communications standards. The term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. In embodiments, the analyte sensor computing device 105 includes a wireless communication module for transmitting to and receiving data, for example for transmitting and receiving data from a network, such as a telecommunications network. In examples, the communication module transmits data, including video data, though a cellular network or mobile network, such as a Global System for Mobile Communications (GSM), General Packet Radio Service (GPRS), cdmaOne, CDMA2000, Evolution-Data Optimized (EV-DO), Enhanced Data Rates for GSM Evolution (EDGE), Universal Mobile Telecommunications System (UMTS), Digital Enhanced Cordless Telecommunications (DECT), Digital AMPS (IS-136/TDMA), and Integrated Digital Enhanced Network (iDEN), Long-Term Evolution (LTE), $3^{rd}$ generation mobile network (3G), 4th generation mobile network (4G), and/or 5th generation mobile network (5G) networks. In embodiments, the computing device 105 is directly connected with one or more devices via the direct wireless connection by using, for example, Bluetooth and/or BLE protocols, WiFi protocols, Infrared Data Association (IrDA)

protocols, ANT and/or ANT+ protocols, LTE ProSe standards, and the like. In embodiments, the communications port is configured to operate in accordance with one or more known wired communications protocol, such as a serial communications protocol (e.g., the Universal Serial Bus (USB), FireWire, Serial Digital Interface (SDI), and/or other like serial communications protocols), a parallel communications protocol (e.g., IEEE 1284, Computer Automated Measurement And Control (CAMAC), and/or other like parallel communications protocols), and/or a network communications protocol (e.g., Ethernet, token ring, Fiber Distributed Data Interface (FDDI), and/or other like network communications protocols).

In embodiments, the analyte sensor computing device 105 is configured to run, execute, or otherwise operate one or more applications. In embodiments, the applications include native applications, web applications, and hybrid applications. For example, the native applications are used for operating the analyte sensor computing device 105, sensor(s) (e.g., sensors 107 at FIG. 1) coupled to the analyte sensor computing device 105, and other like functions of the analyte sensor computing device 105. In embodiments, native applications are platform or operating system (OS) specific or non-specific. In embodiments, native applications are developed for a specific platform using platform-specific development tools, programming languages, and the like. Such platform-specific development tools and/or programming languages are provided by a platform vendor. In embodiments, native applications are pre-installed on analyte sensor computing device 105 during manufacturing, or provided to the analyte sensor computing device 105 by an application server via a network (e.g., network 115 at FIG. 1). Web applications are applications that load into a web browser of the analyte sensor computing device 105 in response to requesting the web application from a service provider. In embodiments, the web applications are websites that are designed or customized to run on a computing device by taking into account various computing device parameters, such as resource availability, display size, touch-screen input, and the like. In this way, web applications may provide an experience that is similar to a native application within a web browser. Web applications may be any server-side application that is developed with any server-side development tools and/or programming languages, such as PHP, Node.js, ASP.NET, and/or any other like technology that renders HTML. Hybrid applications may be a hybrid between native applications and web applications. Hybrid applications may be a standalone, skeletons, or other like application containers that may load a website within the application container. Hybrid applications may be written using website development tools and/or programming languages, such as HTML5, CSS, JavaScript, and the like. In embodiments, hybrid applications use browser engine of the analyte sensor computing device 105, without using a web browser of the analyte sensor computing device 105, to render a website's services locally. In some embodiments, hybrid applications also access computing device capabilities that are not accessible in web applications, such as the accelerometer, camera, local storage, and the like.

Any combination of one or more computer usable or computer readable medium(s) may be utilized with the embodiments disclosed herein. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium can even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computing device, partly on the user's computing device, as a stand-alone software package, partly on the user's computing device and partly on a remote computer or entirely on the remote computer or server. In the latter scenario, the remote computer may be connected to the user's computing device, through any type of network, including a local area network (LAN) or a wide area network (WAN), or the connection may be made to an external computing device, (for example, through the Internet using an Internet Service Provider), or wireless network, such as described above.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium. A code segment may represent a procedure, a function, a subprogram, a program, a routine, a subroutine, a module, program code, a software package, a class, or any combination of instructions, data structures, program statements, and the like.

In various embodiments, an article of manufacture may be employed to implement one or more methods as disclosed herein. The article of manufacture may include a computer-readable non-transitory storage medium and a storage medium. The storage medium may include programming instructions configured to cause an apparatus to practice some or all aspects of a method of calibrating an analyte sensor using a computing device, in accordance with embodiments of the present disclosure.

The storage medium may represent a broad range of persistent storage medium known in the art, including but not limited to flash memory, optical disks or magnetic disks.

The programming instructions, in particular, may enable an apparatus, in response to their execution by the apparatus, to perform various operations described herein. For example, the storage medium may include programming instructions configured to cause an apparatus to practice some or all aspects of a method of conducting calibration of an analyte sensor (e.g., sensor(s) 107 at FIG. 1) using a computing device (e.g., analyte sensor computing device 105 at FIG. 1), in accordance with embodiments of the present disclosure.

Analyte sensing device 107 may comprise an analyte sensing element 114. In some examples, analyte sensing element 114 may comprise one or more wire(s) or electrode(s) for translating an analyte (e.g., glucose) concentration into a representative electrical signal. Analyte sensing device 107 may further comprise a communication module 108 (e.g., transmitter, receiver, or transceiver) for communicating data (wired or wirelessly) and other information over network 115. In some examples, analyte sensing device 107 may further include a microprocessor 112 and a printed circuit board 113, similar to that discussed above for the analyte sensor computing device. Other components of analyte sensing device 107 that are not shown may include one or more of a memory controller, volatile memory (e.g., DRAM), non-volatile memory (e.g., ROM), flash memory, etc.

In some embodiments where CAM system 100 is configured as a CGM system, the system may in some examples include an insulin delivery unit 170. Insulin delivery unit 170 may be comprised of at least three parts, including but not limited to insulin pump 171, tubing 172 and infusion set 173. In an embodiment, insulin pump 171 may be battery powered and may contain (or be fluidically coupled to) an insulin reservoir (e.g., container), a pumping mechanism (e.g., pump driven by a small motor) and one or more buttons and/or touch screen (not shown) to program insulin delivery. In some examples, insulin pump 171 may receive instructions for insulin delivery over network 115, from one of analyte sensor computing device 105 or analyte sensing device 107. The instructions may be based on glucose concentrations as obtained via analyte sensing device 107. In such an example, it may be understood that insulin delivery unit 170 may operate in a closed-loop fashion with other components of CGM system 100 (e.g., analyte sensor computing device 105 and analyte sensing device 107) to mimic the way a pancreas works. It may be understood that each of insulin pump 171, tubing 172 and infusion set 173 may be coupled to each other in order to enable insulin pump 171 to deliver insulin to a subject by way of tubing 172 and infusion set 173. While insulin pump 171 may be battery powered, it may be understood that in some additional or alternative examples insulin pump 171 may be powered by electrically coupling insulin pump 171 to an external power source.

In some examples, insulin pump 171 may include buttons and/or a touch screen (not shown) for programming insulin delivery parameters. In another additional or alternative example, as mentioned above, insulin pump 171 may receive instructions for insulin delivery over network 115. Accordingly, in some examples insulin pump 171 may include a communication module 176 (e.g., receiver, or transceiver) capable of receiving and/or sending information (wired or wirelessly) over network 115, a printed circuit board 174, and a microprocessor 175. Other components of insulin pump 171 that are not shown may include one or more of a memory controller, volatile memory (e.g., DRAM), non-volatile memory (e.g., ROM), flash memory, etc.

Tubing 172 may in some examples comprise a thin tube fluidically coupled to each of the insulin reservoir and infusion set 173. Tubing 172 may be plastic, Teflon™, etc. Infusion set 173 may comprise componentry made of Teflon™ and/or steel, and may attach to skin of a subject by way of an adhesive patch. The infusion set 173 may include a short thin tubing (e.g., cannula) that is inserted to skin via a needle housed within the cannula. After insertion, the needle may be removed and the thin cannula may remain under the skin. It may be understood that the above description relates to an example infusion set, but other similar infusion sets may be used interchangeably without departing from the scope of this disclosure.

Figure 2:
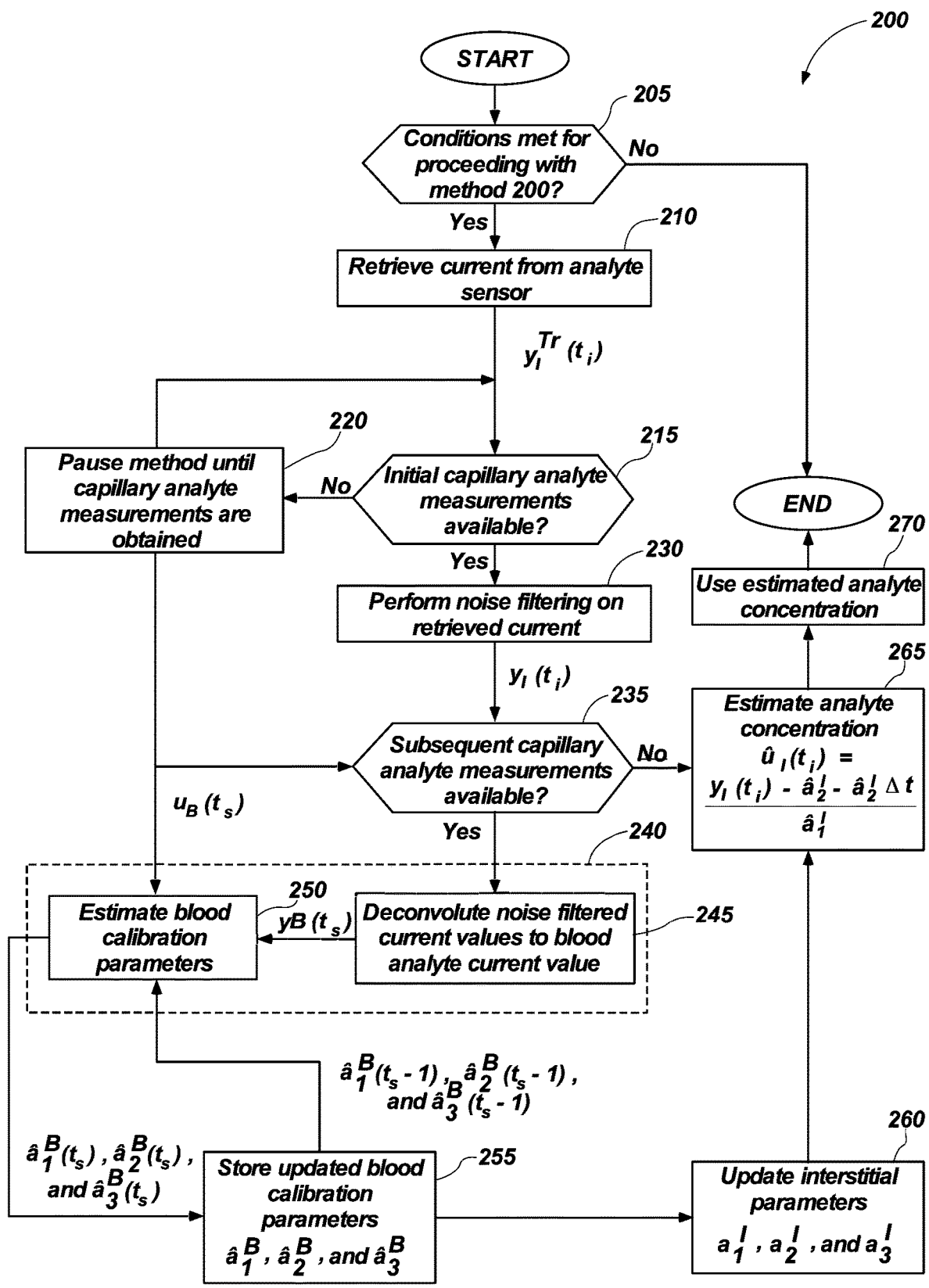
FIG. 2 is a flowchart for a method for estimating an analyte level measured by an analyte sensor of FIG. 1.

Turning now to FIG. 2, an example method 200 is shown for calibrating an analyte sensor (e.g., analyte sensor(s) 107 at FIG. 1) and based on the calibration, determining an analyte value (e.g., amount, level, concentration, etc.). Method 200 may comprise software instructions stored on non-transitory computer readable medium that, when executed by a processor, cause the processor to perform the instructions to calibrate the analyte sensor. As a representative example, the analyte is glucose and the analyte sensor is a glucose sensor, more specifically, a CGM sensor. It may be understood that method 200 is derived at least in part based on the model shown in detail at FIG. 3, and includes steps of calculating particular values/parameters (some variables of which are illustrated near corresponding blocks or steps at FIG. 2) that will be discussed in greater detail following overall description of the methodology of FIG. 2. As such values/parameters and corresponding variables will be discussed in greater detail below following the high level description of the methodology of FIG. 2, specific reference is not made to the variables illustrated at FIG. 2 as part of the high level description. However, the variables serve to orient the reader to various concepts associated with the method of FIG. 2 and discussed herein.

Method 200 begins at 205, and includes indicating whether conditions are met for proceeding with the methodology illustrated at FIG. 2. In some examples, conditions being met at 205 may include a determined amount of time having elapsed since method 200 was previously performed on the same analyte sensor. In another additional or alternative example, conditions being met at 205 may include an indication that the analyte sensor is a recently inserted sensor, and that it is requested that the methodology of FIG. 2 be conducted on the newly inserted sensor. In another additional or alternative example, conditions being met at 205 may include an indication that one or more capillary analyte value(s) (e.g., capillary glucose values) have recently been obtained, for example obtained less than a predetermined timeframe ago (e.g., less than 1 hour ago, less than 45 minutes ago, less than 30 minutes ago, less than 15 minutes ago, less than 10 minutes ago, less than 5 minutes ago, less than 2 minutes ago, less than 1 minute ago, etc.). In another additional or alternative example, conditions being met at 205 may include an indication that the analyte sensor is not providing analyte concentration values that are accurate to within a desired threshold of actual blood analyte values (e.g., capillary blood analyte values measured via a test meter). Such an indication may be made, for example, via comparing analyte values as determined via the analyte sensor with other analyte values determined, for example, via a blood analyte meter.

Figure 4:
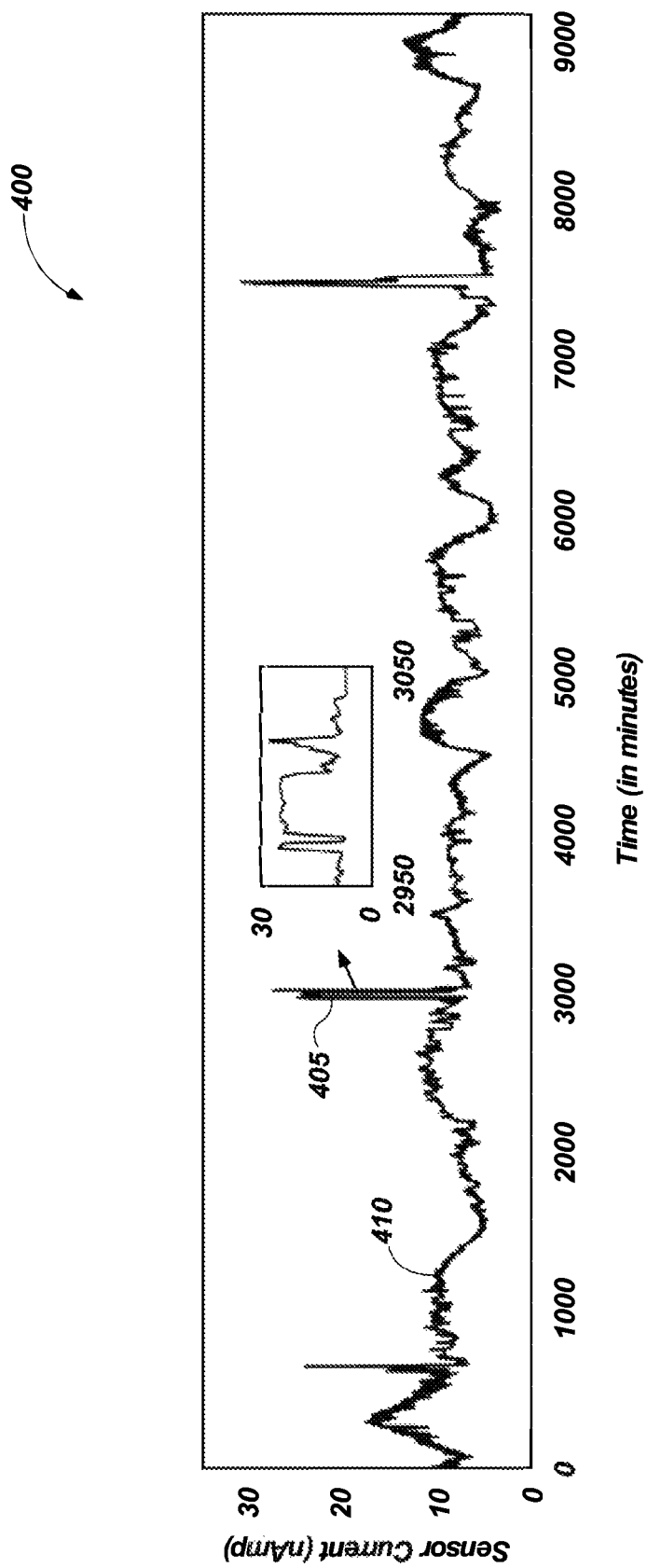
FIG. 4 is a graph showing a sample current signal generated by a glucose sensor. The graph illustrates high frequency low magnitude noise and low frequency high magnitude noise.

If, at 205, conditions are not indicated to be met for conducting the methodology of FIG. 2, method 200 may end. Alternatively, responsive to conditions being met at 205, method 200 proceeds to 210. At 210, method 200 includes retrieving current values from the analyte sensor over a predetermined time duration. These current measurements can be continuous or at discrete points, for example, during the predetermined time duration. It may be understood that the current obtained at 210 may be noisy, for example comprising both high frequency low magnitude noise and low frequency higher magnitude noise components. Turning briefly to FIG. 4, graph 400 depicts an example noisy current that may be obtained at 210. Graph 400 plots sensor current against time, and includes an inset to illustrate the low frequency higher magnitude noise components 405, as compared to the high frequency lower magnitude noise 410.

Returning to FIG. 2, responsive to the current being retrieved from the analyte sensor, method 200 proceeds to 215. At 215, the method determines if a blood analyte value, such as a capillary glucose value, is available to calibrate the received current values. In some examples, the blood analyte value may be a first blood analyte value obtained subsequent to sensor insertion. However, in other examples, the blood analyte value may not be the first, but instead may comprise a value obtained subsequent to the first blood analyte value having been obtained post sensor insertion. It may be understood that the calibration methodology of FIG. 2 may be performed each time that a new blood analyte value is obtained.

At block 215, if it is determined that no blood analyte value (e.g., no new blood analyte value) is available to calibrate the received current values, the method proceeds to 220, where method 200 pauses until the blood analyte value is available to calibrate the received current values. A blood analyte value may not be available if a blood analyte value has not been received within a predetermined time duration of the query, for example.

Returning to step 215, responsive to an indication that there is a blood glucose value (e.g., $1^{st}$ capillary glucose value, or newly obtained capillary glucose value) available to calibrate the received current values, then this blood glucose value is used for subsequent steps of method 200. Briefly, the blood analyte value is available to use for deconvolution in block 245 and parameter estimation in block 250 of the calibration step in block 240, as discussed below. Once the blood analyte value is available, the method proceeds to noise filtering in block 230.

In block 230 the analyte sensor current values are noise filtered. The noise in the current values from a given sensor can be broken down into two components that can be separately filtered. These two components are the low frequency noise attributed to physical disturbances on the sensor (e.g., physical pressure on the sensor, sensor movement attributable to exercise, or sensor dislodging) and high frequency low magnitude noise attributed to sensor measurement noise. In embodiments, the noise due to physical disturbances on the sensor is filtered out, for example using heuristic rules to detect and filter the low frequency noise with high magnitude that is attributed to the physical disturbances on the sensor. Briefly, sensor measurements outside of a desired or threshold range (e.g., greater than 60 nAmp or less than 0.5 nAmp) may in some examples be filtered out. For the heuristic filtering, the sensor current may be taken as the mean of previous measurements over a predetermined time period (e.g. 3 hours, 2 hours, 1 hour, etc.), as an example. Additionally or alternatively, sensor measurements may be considered outside the desired range, or in other words, erroneous or indicative of sensor degradation or general loss of sensitivity, responsive to the measurement(s) being greater than twice the mean of an immediately prior 10 minute measurement period. In such an example, the modified or filtered sensor current may be taken as a mean of the immediately prior 10 minute measurement period.

In embodiments, the high frequency low magnitude sensor measurement noise is filtered out by application of Kalman filtering. As one example, the low frequency higher magnitude noise is filtered first, followed by filtering of the high frequency lower magnitude noise, in sequential fashion. As another example, the high frequency lower magnitude noise is filtered first, followed by filtering of the low frequency higher magnitude noise. Simultaneous filtering of both the high frequency low magnitude and low frequency high magnitude noise is also within the scope of this disclosure.

Following noise filtering of the retrieved sensor current at block 230, method 200 proceeds to 235. At block 235 the method queries if a subsequent, i.e. $2^{nd}$, $3^{rd}$, $4^{th}$, etc., capillary glucose value is available. If there is not a subsequent, i.e. $2^{nd}$, $3^{rd}$, $4^{th}$, etc. capillary glucose value available for calibration, the noise filtered current can be used to estimate the glucose concentration in block 265. Then, method 200 may proceed to 270, where the estimated glucose concentration can be passed on, for example to a display device (e.g., touchscreen 110 associated with analyte sensor computing device 105 at FIG. 1), insulin delivery system (e.g., insulin delivery system 170 at FIG. 1), or other networked device to be. Briefly, it may be understood that capillary analyte values may be available at an interval. The interval may be approximately 12 hours, however the interval may be greater than or less than 12 hours (e.g., 24 hours), without departing from the scope of this disclosure. Accordingly, it may be understood that the current-to-glucose transformation model is updated via the methodology of FIG. 2 every, for example, 12-24 hours, and this updated modeling is assumed to be valid until a subsequent capillary analyte value is obtained. However, the current is available every minute, and accordingly is continuously and regularly transformed to glucose level using the last updated modeling. Accordingly, it may be understood that with every current reading (e.g., approximately every minute), method 200 determines whether a new capillary analyte value is available. If not, then the last updated model is used for transforming the current to glucose level. However, if available, then the new capillary analyte value is used to update the current-to-glucose transformation model per the methodology of FIG. 2 elaborated further below. If, for some reason a particular capillary analyte value cannot be used, then it may be understood that the user may be requested to take an additional capillary analyte value reading within a set time frame (e.g., within 10 minutes).

If an appropriate capillary analyte value is available at 235, the method proceeds to 240. Specifically, block 240 includes performing calibration of the noise filtered current signal using the subsequent, i.e. $2^{nd}$, $3^{rd}$, $4^{th}$, etc. capillary glucose value(s), by a process of deconvolution in block 245 and parameter estimation in block 250.

Figure 5:
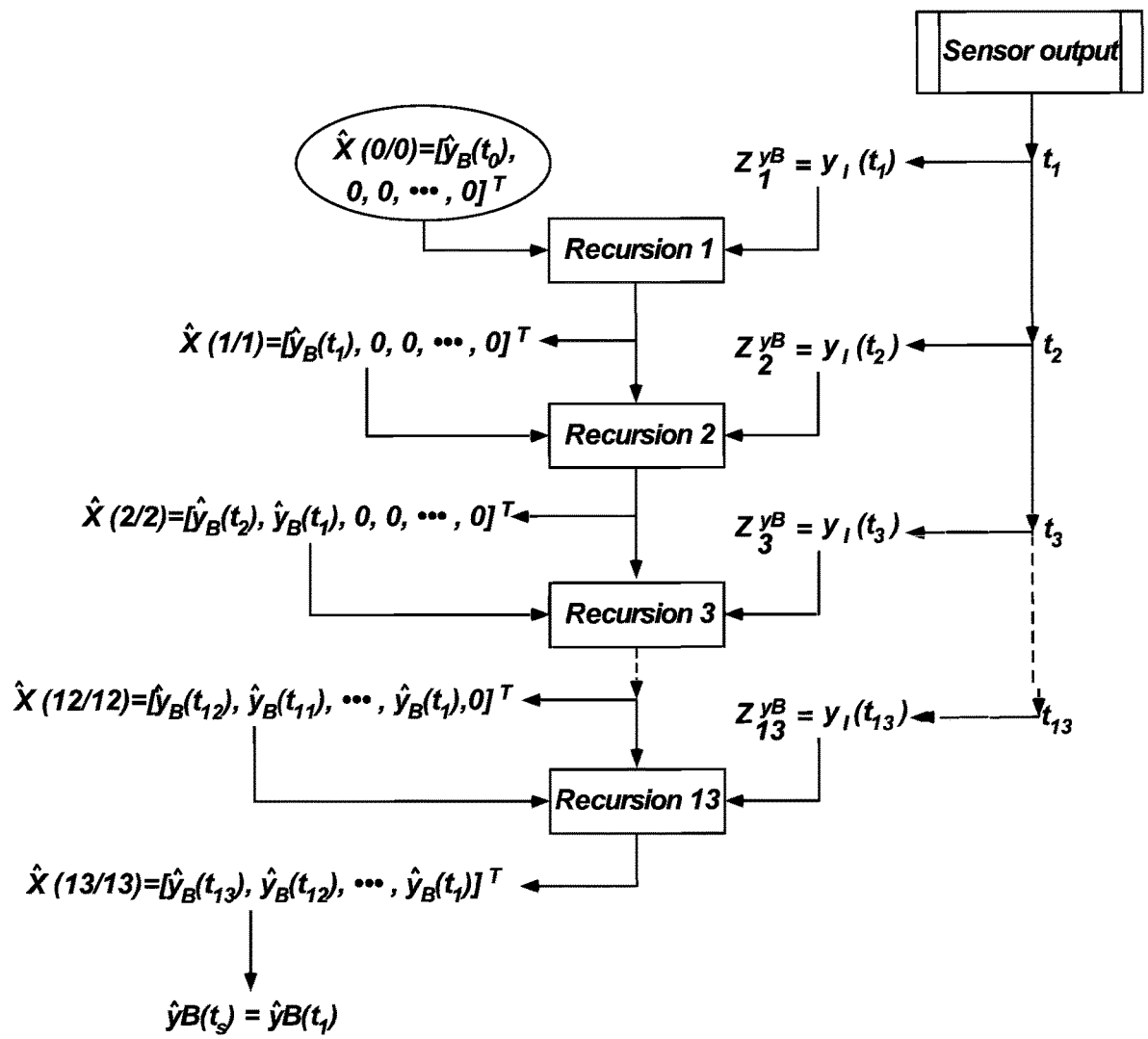
FIG. 5 depicts an example of a sequential Kalman filter as used in accordance with the method of FIG. 2.

In block 245, the noise filtered current values are deconvoluted to blood glucose current value using Kalman-based deconvolution. In embodiments, the Kalman-based deconvolution uses a sequential Kalman filter (refer to FIG. 5 for an example sequential Kalman filter). In embodiments, the sequential Kalman filter is implemented over a time period prior to the calibration time sufficient for convergence, for example, using noise filtered sensor current values collected in a time window of between about 30 minutes and 120 minutes, such as a 60 minute time window prior to the calibration time. In embodiments, within this time window a sampling interval of between about 1 minute and about 15 minutes may be used, such as 5 minutes. In embodiments, the sequential Kalman filter includes between about 5 and about 20 recursions of the filter implementation, such as 13 recursions of the filter implementation. It is contemplated the method can include as many recursions of the filter implementation as necessary for convergence.

In block 250 the blood calibration parameters are estimated using a Kalman filter. In embodiments where the analyte sensor should estimate the analyte levels immediately after the first calibration and there is not enough convergence time for the Kalman filter (i.e. the calibration parameters state is only updated once) the initial estimate and covariance can be computed offline using training datasets (e.g., by utilizing a cubature Kalman filter, as will be discussed in greater detail below).

In block 255, the updated blood calibration parameters are stored.

In block 260, the interstitial parameters are updated based on the blood calibration parameters, as will be described in greater detail below.

Responsive to the interstitial parameters being updated at 260, method 200 proceeds to 265. At block 265, the blood analyte levels are estimated based on the interstitial parameters (step 260) and the noise filtered current (step 230). The blood analyte value(s) may be passed on, for example to a display device (e.g., touchscreen 110 associated with analyte sensor computing device 105 at FIG. 1), insulin delivery system (e.g., insulin delivery system 170 at FIG. 1) (where applicable), or other networked device, to be used. For example, in a situation where the analyte sensor is a glucose sensor, and where the analyte is glucose, method 200 may include computing an amount of insulin to be provided to the subject based on the determined blood analyte value(s). In one example, the computed insulin amount may be sent, along with one or more instructions, to the insulin delivery system so that an insulin pump may be controlled to deliver the desired amount of insulin. In another related example, the computed insulin amount may be displayed on a screen associated with, for example, a computing device (e.g., analyte sensor computing device 105 at FIG. 1) associated with the analyte sensor.

While particular reference is given to glucose as a model analyte, the methods, apparatuses, tangible media, and systems disclosed herein are applicable for any analyte sensor that has been inserted into the tissue of a subject. Other sensors that can be used with the methods, apparatuses, tangible media, and systems are, without limitation, sensors for the detection of albumin, alkaline phosphatase, alanine transaminase, aspartate aminotransferase, bilirubin, blood urea nitrogen, calcium, carbon dioxide ($CO_2$), chloride, creatinine, glucose, gamma-glutamyl transpeptidase, hematocrit, lactate, lactate dehydrogenase, magnesium, oxygen, pH, phosphorus, potassium, sodium, total protein, uric acid, metabolic markers, and drugs. Other analytes are contemplated as well, including but not limited to acetaminophen, dopamine, ephedrine, terbutaline, ascorbate, uric acid, oxygen, d-amino acid oxidase, plasma amine oxidase, xanthine oxidase, reduced nicotinamide adenine dinucleotide phosphate (NADPH) oxidase, alcohol oxidase, alcohol dehydrogenase, pyruvate dehydrogenase, diols, ROS (reactive oxygen species), nitric oxide (NO), cholesterol, triglycerides, gentisic acid, ibuprophen, L-Dopa, methyl dopa, salicylates, tetracycline, tolazamide, tolbutamide, acarboxyprothrombin, acylcarnitine, adenine phosphoribosyl transferase, adenosine deaminase, albumin, alpha-fetoprotein, amino acid profiles (arginine (Krebs cycle), histidine/urocanic acid, homocysteine, phenylalanine/tyrosine, tryptophan); andrenostenedione, antipyrine, arabinitol enantiomers, arginase, benzoylecgonine (cocaine), biotinidase, biopterin, c-reactive protein, carnitine, carnosinase, cluster of differentiation 4 (CD4), ceruloplasmin, chenodeoxycholic acid, chloroquine, cholinesterase, conjugated 1-β hydroxy-cholic acid, cortisol, creatine kinase, creatine kinase MM isoenzyme, cyclosporin A, d-penicillamine, de-ethylchloroquine, dehydroepiandrosterone sulfate, DNA (deoxyribonucleic acid); alcohol dehydrogenase, alpha 1-antitrypsin, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, human cytomegalovirus (HCMV), human immunodeficiency-1 (HIV-1), human T-cell leukemia virus type 1 (HTLV-1), Leber hereditary optic neuropathy, RNA (ribonucleic acid), phenylalanine, *Plasmodium vivax,* 21-deoxycortisol, desbutylhalofantrine, dihydropteridine reductase, diptheria/tetanus antitoxin, erythrocyte arginase, erythrocyte protoporphyrin, esterase D, fatty acids/acylglycines, free β-human chorionic gonadotropin, free erythrocyte porphyrin, free thyroxine (FT4), free tri-iodothyronine (FT3), fumarylacetoacetase, galactose/gal-1-phosphate, galactose-1-phosphate uridyltransferase, gentamicin, glucose-6-phosphate dehydrogenase, glutathione, glutathione perioxidase, glycocholic acid, glycosylated hemoglobin, halofantrine, hemoglobin variants, hexosaminidase A, human erythrocyte carbonic anhydrase I, 17-alpha-hydroxyprogesterone, hypoxanthine phosphoribosyl transferase, immunoreactive trypsin, lactate, lead, lipoproteins ((a), B/A-1, β), lysozyme, mefloquine, netilmicin, phenobarbitone, phenyloin, phytanic/pristanic acid, progesterone, prolactin, prolidase, purine nucleoside phosphorylase, quinine, reverse tri-iodothyronine (rT3), selenium, serum pancreatic lipase, sissomicin, somatomedin C, specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica,* enterovirus, *Giardia duodenalisa, Helicobacter pylori,* hepatitis B virus, herpes virus, HIV-1, IgE (atopic disease), influenza virus, middle Eastern respiratory syndrome (MERS), severe acute respiratory syndrome (SARS)-coronavirus (CoV), SARS-CoV-2, *Leishmania donovani,* leptospira, measles/mumps/rubella, *Mycobacterium leprae, Mycoplasma pneumoniae,* Myoglobin, *Onchocerca volvulus,* parainfluenza virus, *Plasmodium falciparum,* poliovirus, *Pseudomonas aeruginosa,* respiratory syncytial virus, *rickettsia* (scrub typhus), *Schistosoma mansoni, Toxoplasma gondii, Trepenoma pallidium, Trypanosoma cruzi/rangeli,* vesicular stomatis virus, *Wuchereria bancrofti,* yellow fever virus), specific antigens (hepatitis B virus, HIV-1), succinylacetone, sulfadoxine, theophylline, thyrotropin (TSH), thyroxine (T4), thyroxine-binding globulin, trace elements, transferrin, UDP-galactose-4-epimerase, urea, uroporphyrinogen I synthase, vitamin A, white blood cells, and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin, ethanol, cannabis (marijuana, tetrahydrocannabinol, hashish), inhalants (nitrous oxide, amyl nitrite, butyl nitrite, chlorohydrocarbons, hydrocarbons), cocaine (crack cocaine), stimulants (amphetamines, methamphetamines, Ritalin, Cylert, Preludin, Didrex, PreState, Voranil, Sandrex, Plegine), depressants (barbituates, methaqualone, tranquilizers such as Valium, Librium, Miltown, Serax, Equanil, Tranxene), hallucinogens (phencyclidine, lysergic acid, mescaline, peyote, psilocybin), narcotics (heroin, codeine, morphine, opium, meperidine, Percocet, Percodan, Tussionex, Fentanyl, Darvon, Talwin, Lomotil), designer drugs (analogs of fentanyl, meperidine, amphetamines, methamphetamines, and phencyclidine, for example, Ecstasy), anabolic steroids, and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), histamine, Advanced Glycation End Products (AGEs) and 5-hydroxyindoleacetic acid (FHIAA).

Problem Formulation

Figure 3:
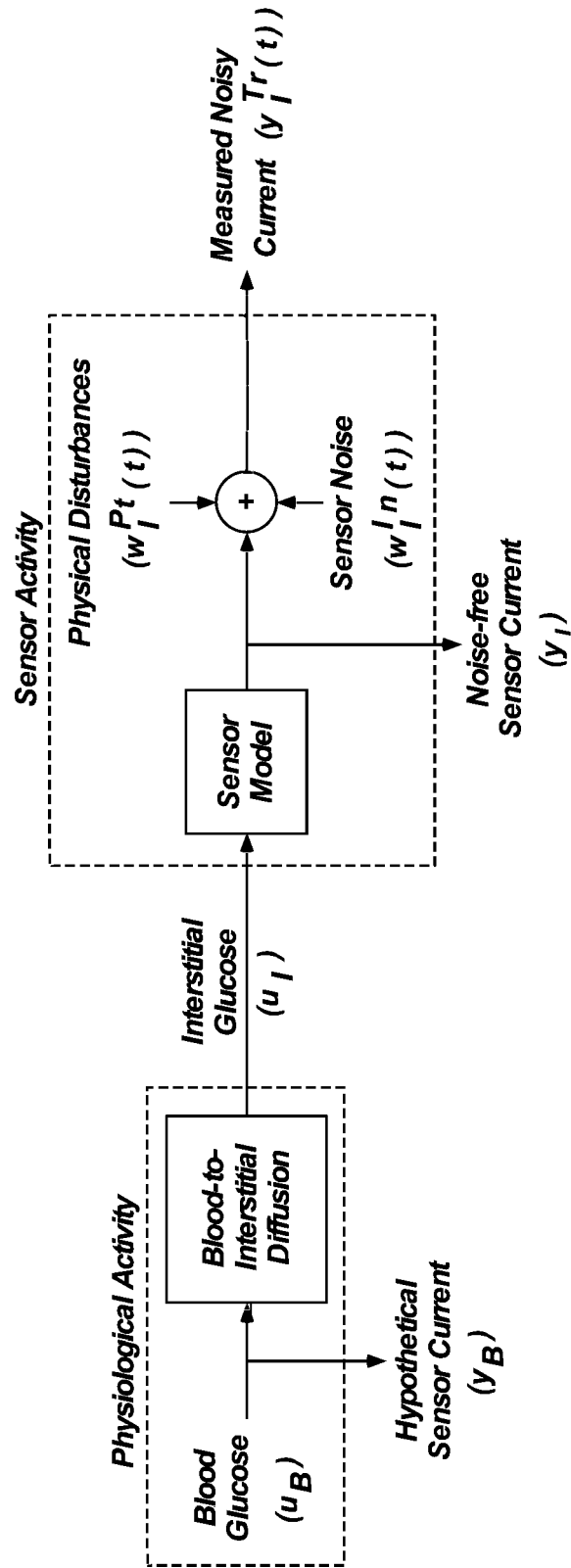
FIG. 3 is a block diagram showing a model showing a relationship between blood glucose concentration and analyte sensor current measurements.

As mentioned above, the method of FIG. 2 is derived from the model depicted at FIG. 3. In terms of this discussion, reference is made to a glucose sensor, where the analyte is glucose, for clarity. With regard to Equation (1) below, let $y_I(t)$ be the sensor-generated noise-free electrical current and $u_I(t)$ be the interstitial glucose level. The objective is to determine $u_I(t)$ from $y_I(t)$ using the model of FIG. 3:

$$y_I(t) = a_1^I \cdot u_I(t) + a_2^I + a_3^I \cdot \Delta t \quad (1)$$

where $\{a_1^I, a_2^I \text{ and } a_3^I\}$ are interstitial calibration parameters (refer to step 260 of method 200) and $\Delta t$ is the time since sensor insertion. Thus, the problem is to estimate the interstitial calibration parameters $\{a_1^I, a_2^I \text{ and } a_3^I\}$. Estimating the calibration parameters faces two challenges: (i) $y_I(t)$ cannot be measured directly; instead a distorted version of $y_I(t)$ is measured with high- and low-frequency noise, and (ii) the sensor response varies with sensor age, and the time-variability is patient- and sensor-dependent. Thus, $\{a_1^I, a_2^I \text{ and } a_3^I\}$ are updated periodically using intermittent capillary glucose measurements.

Let $u_B(t)$ be the intermittent capillary glucose measurement and $y_B(t)$ be a hypothetical sensor current if the sensor was inserted in the blood instead of the interstitial fluid. Assuming the sensor has the same dynamics in the interstitial fluids and blood, $y_B(t)$ is related to $u_B(t)$ by Equation (2):

$$y_B(t) = a_1^B \cdot u_B(t) + a_2^B + a_3^B \cdot \Delta t \quad (2)$$

where $\{a_1^B, a_2^B \text{ and } a_3^B\}$ are blood calibration parameters. It can be shown that the blood calibration parameters are related to the interstitial calibration parameters by the following Equations (3):

$$a_1^I = a_1^B,\ a_2^I = a_2^B - a_3^B \cdot \tau \text{ and } a_3^I = a_3^B \quad (3)$$

Thus, the calibration problem can be solved by estimating $\{a_1^B, a_2^B \text{ and } a_3^B\}$. Note that $y_B(t)$ can be determined from $y_I(t)$ by deconvolution with $h(t) = \tau^{-1} e^{-t/\tau}$, assuming first order diffusion dynamics where $\tau$ is the time constant of glucose diffusion from the blood to the interstitial fluid.

Real-Time Glucose Estimation

The glucose estimation method includes three steps:
(A) noise filtering,
(B) estimation of calibration parameters,
(C) estimation of blood glucose level.

The disclosed method utilizes Kalman filtering in the first two steps.

Summary of Kalman Filter

The Kalman filter operates over a linear dynamical state space model defined by Equation (4) and Equation (5):

$$x_k = F_k x_{k-1} + w_k \quad (4)$$

$$z_k = H_k x_k + v_k \quad (5)$$

where $X_k \in \Re^n$ and $z_k \in \Re^d$ are state and measurement vectors, respectively, at $k^{th}$ instant of time, $F_k$ and $H_k$ are constants matrices with appropriate dimensions, and $w_k$ and $v_k$ are process and measurement noises, respectively. $w_k$ and $v_k$ are assumed to be Gaussian with zero mean and covariances $Q_k$ and $R_k$, respectively. The Kalman filter estimates the elements of $X_k$ using the observed quantities $z_k$.

The Kalman filter includes two steps; prediction and update.

Prediction: This step determines the prior state estimate ($\hat{X}_{k|k-1}$) and the state covariance ($P_{k|k-1}$) via Equation (6):

$$\hat{x}_{k|k-1} = F_k \hat{x}_{k-1|k-1}$$

$$P_{k|k-1} = F_k P_{k-1|k-1} F_k^T + Q_k \quad (6)$$

Update: In this step, the posterior state estimate, $\hat{X}_{k|k}$, and covariance, $P_{k|k}$, are computed after a new measurement of z_k is available. Prior to computing $\hat{X}_{k|k}$ and $P_{k|k}$, the innovation vector ($\tilde{y}_{k|k-1}$), the innovation covariance ($S_k$), and the Kalman gain ($K_k$) are computed as:

$$\tilde{y}_{k|k-1} = z_k - H_k \hat{x}_{k|k-1}$$

$$S_k = H_k P_{k|k-1} H_k^T + R_k$$

$$K_k = P_{k|k-1} H_k^T (S_k)^{-1} \quad (7)$$

Subsequently, $\hat{X}_{k|k}$ and $P_{k|k}$ are computed as:

$$\hat{x}_{k|k} = \hat{x}_{k|k-1} + K_k \tilde{y}_{k|k-1} \quad (8)$$

$$P_{k|k} = (I - K_k H_k) P_{k|k-1} \quad (9)$$

It may be understood that the initial state estimate ($\hat{X}_{0|0}$) and covariance ($P_{0|0}$) may be assigned arbitrarily since they converge to the true values over time. However, if high accuracy is desired at the start of the filter operation, then $\hat{X}_{0|0}$ and covariance $P_{0|0}$ may be assigned precisely.

Noise Filtering

Assuming additive noises, the measured electrical current $y_I^{Tr}(t)$ can be written as $$y_I^{Tr}(t) = y_I(t) + w_I^{In}(t) + w_I^{Pt}(t) \quad (10)$$

where $w_I^{In}(t)$ is a sensor measurement noise and $w_I^{Pt}(t)$ is a noise due to physical disturbances on the sensor (e.g., physical pressure on the sensor or sensor dislodging). Typically, $w_I^{In}(t)$ is a high frequency signal with low magnitude and $w_I^{Pt}(t)$ is a low frequency noise with high magnitude. As mentioned above, FIG. 4 shows a sample noisy current signal that includes both the higher magnitude, lower frequency noise (plot 405 at FIG. 4) and the lower magnitude, higher frequency noise (plot 410 at FIG. 4).

A set of heuristic rules were implemented to detect and filter $w_I^{Pt}(t)$. The resultant current $y_{I_b}^{Tr}(t)$ according to Equation (11) is:

$$y_{I_b}^{Tr}(t) = y_I(t) + w_I^{In}(t) \quad (11)$$

The remaining noise $w_I^{In}(t)$ is filtered by implementing a Kalman filter. The state and measurement variables of the Kalman filter are defined as $X_k^{y_I} = y_I(t_k)$, and $Z_k^{y_I} = y_{I_b}^{Tr}(t)$ respectively. The sampling interval is only 1 minute, hence a random walk model defines the state dynamics according to Equation (12):

$$x_k^{yI} = x_{k-1}^{yI} + w_{k-1}^{yI} \quad (12)$$

where $w_I^{yI}$ is a process noise added to compensate the slight current variation from $t_{k-1}$ to $t_k$.

Replacing $y_I(t_k)$ with $X_k^{yI}$ and $y_{I_b}^{Tr}(t_k)$ with $z_k^{yI}$ in Equation (11), the measurement model would be:

$$z_k^{yI} = x_k^{yI} + v_k^{yI} \quad (13)$$

where $v_k^{yI} = w_I^{In}(t_k)$.

The outcome of Kalman filter (Equations (6)-(9)), implemented over Equations (12) and (13), is $\hat{X}_{k|k} = \hat{y}_I(t_k)$, which is the estimate of $y_I(t_k)$.

Estimation of Calibration Parameters

The calibration parameters $\{a_1', a_2' \text{ and } a_3'\}$ are updated when a new capillary glucose measurement becomes available (around once or less per day; calibration times are denoted as $t_s$). The calibration parameters are estimated following a two-step process.

$y_B(t_s)$ Estimation $y_B(t_s)$ can be estimated by deconvoluting $y_I(t)$ over $h(t)$ at $t=t_s$. A direct inverse solution of the deconvolution problem is notoriously difficult to implement because of its well-known inherent ill-conditioning. The ill-conditioning can be mitigated by regularization, but it requires the solution of complex integrals, which can be computationally demanding. To reduce the computational burden, a modified Kalman-based approach is herein implemented, which relies on a sequential Kalman filter (see FIG. 5 as an example).

To ensure the convergence of the sequential Kalman filter, it was implemented over 60-min time window prior to the calibration time (i.e. ($t_s$−60) to $t_s$). A sampling interval of 5 minutes was used which results in 13 samples and hence 13 recursions of the filter implementation. The sequential Kalman filter adds a new state at every recursion as follows: $\{y_B(t_1)\}$ at $t_1$, $\{y_B(t_2); y_B(t_1)\}$ at $t_2$, . . . , $\{y_B(t_{13}); y_B(t_{12}); \ldots ; y_B(t_2)\}$ at $t_{13}$. For implementation simplicity, the state variable was assumed to be 13-dimensional at all recursions by assuming 0 values in the extra dimensions. Therefore, the 13-dimensional state variable at $j^{th}$ recursion is formulated as $X_j^{yB} = [y_B(t_j), y_B(t_{j-1}), \ldots, y_B(t_1), 0, 0, \ldots, 0]^T$ where $j\{1, 2, \ldots 13\}$ and $t_j - t_{j-1} = 5$.

The state dynamics can be represented by a random walk model:

$$x_j^{yB} = x_{j-1}^{yB} + w_{j-1}^{yB} \quad (14)$$

where $w_j^{yB}$ is process noise (13-dimensional vector) added to compensate the possible changes in $y_B(t)$ from $t_{j-1}$ to $t_j$. The process noise is assumed to be Gaussian with zero mean and covariance $Q_j^{yB}$.

The measurement was considered to be the filtered sensor current, i.e. $Z_j^{yB} = y_I(t_j)$. The measurement model follows a linear structure $$z_j^{yB} = H_j^{yB} x_j^{yB} + v_j^{yB} \quad (15)$$

where $H_j^{yB}$ is transition matrix and $v_j^{yB}$ is Gaussian noise with zero mean and covariance $R_j^{yB}$. Following the discussion in the problem formulation, $y_I(t)$ is related to $y_B(t)$ through the impulse response $h(t) = t^{-1} e^{-t/\tau}$. Alternatively, we can say that $Z_j^{yB}$ is related to $X_j^{yB}$ through $h(t)$. Thus, we can determine $H_j^{yB}$ by matrix representation of discretized $h(t)$ (P. Rousseaux and J. Troquet, "Deconvolution of time-varying systems by Kalman filtering: its application to the computation of the active state in the muscle," Sign. Proc., vol. 10, no. 3, pp. 291-301, April 1986).

The sequential Kalman filter outcome after the 13th recursion is $\hat{X}_{13}^{yB} = [\hat{y}_B(t_{13}); \hat{y}_B(t_{12}); \ldots ; y_B(t_1)]^T$. The desired estimate at the calibration time is $\hat{y}_B(t_s) = \hat{y}_B(t_1)$. A flowchart of the sequential Kalman filter is presented in FIG. 5.

Parameter Estimation

The blood calibration parameters are estimated using a Kalman filter with a state defined as $X_s^{BCP} = [a_1^B, a_2^B, a_3^B]^T$. A random walk model characterizes the state dynamics:

$$x_s^{BCP} = x_{s-1}^{BCP} + w_{s-1}^{BCP} \quad (16)$$

where $w_s^{BCP}$ is zero mean Gaussian noise added to compensate the possible changes in the parameters between calibrations points. The measurement variable is set to be the deconvoluted current, $z_s^{BCP} = \hat{y}_B(t_s)$. Following Equation (2), the measurement can be written as $$z_s^{BCP} = H_s^{BCP} x_s^{BCP} + v_s^{BCP} \quad (17)$$

where $H_s^{BCP} = [u_B(t_j) \; 1 \; \Delta t]$ and $v_s^{BCP}$ is noise added to account for the error incurred during the estimation of $y_B(t_s)$. The noise is assumed to be zero mean Gaussian with covariance $R_s^{BCP}$.

The outcomes of Kalman filter, implemented over (16) and (17), are the new estimates of the blood calibration parameters, $\hat{X}_s^{BCP} = [\hat{a}_1^B, \hat{a}_2^B, \hat{a}_3^B]^T$. The estimates of the interstitial calibration parameters $\{a_1', a_2', a_3'\}$ are then calculated based on Equation (3) as shown by Equation (18):

$$\hat{a}_1' = \hat{a}_1^B, \; \hat{a}_2' = \hat{a}_2^B - \hat{a}_3^B \cdot \tau \text{ and } \hat{a}_3' = \hat{a}_3^B \quad (18)$$

The glucose sensor should estimate the glucose levels immediately after the first calibration. Therefore, the Kalman filter does not have enough convergence time (the calibration parameters state is only updated once), and hence a precise knowledge of the initial estimate ($\hat{X}_{0|0}^{BCP}$) and covariance ($P_{0|0}^{BCP}$) is needed. The initial estimate and covariance were computed offline using training datasets (refer to the section "Estimation of $\hat{X}_{0|0}^{BCP}$ and covariance $P_{0|0}^{BCP}$").

Estimation of Glucose Concentration

An inverse implementation of Equation (1) estimates blood glucose levels from the filtered sensor electrical current:

$$\hat{u}_I(t) = \frac{y_I(t)\hat{a}_2^I - \hat{a}_3^I \cdot \Delta t}{\hat{a}_1^I} \quad (19)$$

A high-level flowchart for estimating $u_I(t)$ at $t=t_i$ is provided in FIG. 2.

Database and Model Training

Database

Data for the database was collected from 16 patients with type 1 diabetes. Fourteen patients wore two sensors, one on the left side and another on the right side of the abdomen, while the remaining 2 patients started with two sensors but had one sensor removed before the end of the study. Thus, the two remaining patients were left with a single sensor at the end of the study. Data for each subject was collected for 7 days (e.g., 7 days of data collection each for each subject). Subsequently, 30 datasets were available for the analysis. The datasets are comprised of sensor electrical current, two capillary glucose measurements per day (for calibration), and reference glucose measurements on days 1, 4, and 7. The reference glucose measurements were obtained every 15 minutes in 12-hour clinical sessions on days 1, 4, and 7. The reference glucose measurements were performed using Yellow Spring Instrument (YSI), OH, USA.

The 30 datasets were divided in two sets, a training set of 10 datasets and a test set with 20 datasets. The training set was used to determine the initial estimate and covariance, $\hat{X}_{010}^{BCP}$ and $P_{010}^{BCP}$ to initialize the Kalman filter.

Estimation of $\hat{X}_{010}^{BCP}$ and Covariance $P_{010}^{BCP}$

Using $y_I(t)$ (filtered electrical current) and $u_B(t)$ (reference glucose values) on day 1 of the training datasets, $\hat{X}_{010}^{BCP}$, $P_{010}^{BCP}$, and $\tau$ were estimated to initialize the Kalman filter. Blood calibration parameters $\{a_1^B, a_2^B, a_3^B\}$ and $\tau$ were estimated for each individual dataset (denoted as $\{\hat{a}_1^B, \hat{a}_2^B, \hat{a}_3^B, \hat{\tau}\}$, then $\hat{X}_{010}^{BCP}$ and $P_{010}^{BCP}$ were calculated as the sample mean and sample covariance of $\{\hat{a}_1^B, \hat{a}_2^B, \hat{a}_3^B\}$ over the datasets and t as the sample mean of $\hat{\tau}$ over the datasets.

Beginning with Equation (1) which establishes the relationship between $y_I(t)$. and $u_I(t)$, as the available data are $y_I(t)$ and $u_B(t)$, Equation (1) is written as:

$$y_I(t) = a_1' \cdot (u_B(t) \otimes (1/\tau e^{-t/\tau})) + a_2' + a_3' \cdot \Delta t \quad (20)$$

by replacing $u_I(t)$ with:

$$u_I(t) = u_B(t) \otimes h(t) = u_B(t) \otimes \left(\frac{1}{\tau} e^{-t/\tau}\right) \quad (21)$$

where $\otimes$ represents convolution.

Since $y_I(t)$ and $u_B(t)$ are known, $\{\hat{a}_1^B, \hat{a}_2^B, \hat{a}_3^B\}$ an can be obtained by implementing a parameter estimation scheme over the nonlinear model in Equation (20). The Kalman filter-based parameter estimation discussed earlier cannot be used due to model nonlinearity. However, the same idea can be used (i.e., using filtering as a parameters estimation method) by replacing the ordinary Kalman filter with a nonlinear filter. Several nonlinear filters were implemented, and it was found the most promising results with a cubature Kalman filter (comparisons not shown).

Similar to the ordinary Kalman filter, the cubature Kalman filter is implemented over a dynamic state space model. To this regard, the state and measurement variables were defined as $x^P = [a_1' a_2' a_3' \tau]^T$ and $z_k^P = y_I(t_k)$, respectively. The state dynamics can be represented by a random walk model:

$$x_k^P = x_{k-1}^P + w_k^P \quad (22)$$

where $X_k^P$ is noise, $k \in \{1, 2, \ldots, N_{D1}\}$ and $N_{D1}$ is the number of reference glucose measurements on Day 1. Following (20), the measurement model is formulated as $$z_k^P = x_k^P(1) \cdot \left(u_B(t_k) \otimes \left(\frac{1}{x_k^P(4)} e^{-t_k/x_k^P(4)}\right)\right) + x_k^P(2) + x_k^P(3) \cdot \Delta t + v_k^P \quad (23)$$

where $v_k^P$ is measurement noise. The output of the cubature Kalman filter, implemented over equations (22) and (23), is $\hat{X}_k^P = [\hat{a}_1^{Ik}, \hat{a}_2^{Ik}, \hat{a}_3^{Ik}, \hat{\tau}_k]^T$, $k \in [1; N_{D1}]$. The estimates $\{\hat{a}_1^B, \hat{a}_2^B, \hat{a}_3^B\}$ are obtained as the mean of the last 10 values of $\hat{X}_k^P$ (i.e., $k \in (N_{D1}-9, N_{D1}]$). The estimates $\{\hat{a}_1^B, \hat{a}_2^B, \hat{a}_3^B\}$ of each dataset were obtained from $\{\hat{a}_1', \hat{a}_2', \hat{a}_3'\}$ using equation (3). The sample mean and sample covariance of $\{\hat{a}_1^B, \hat{a}_2^B, \hat{a}_3^B\}$, computed over all training datasets, return $\hat{X}_{010}^{BCP}$ and $P_{010}^{BCP}$ Similarly, mean of $\hat{\tau}$ over all training patients return tau (which was obtained as 5.4 seconds).

Implementation and Results

The developed method was implemented in Matlab 2017 on a personal computer with i3, 2.00 GHz processor, 4 GB RAM, and 64-bit Windows operating system. The performance analysis is based on mean absolute relative difference (MARD) between the estimated glucose and reference glucose measurements. MARD is defined as:

$$MARD = \frac{1}{n}\sum_{i=1}^{n}\left\{100 \cdot \frac{|u_B(t_i) - \hat{u}_B(t_i)|}{u_B(t_i)}\right\} \quad (24)$$

where $u_B(t_1), u_B(t_2), \ldots, u_B(t_n)$ are the reference glucose measurements and $\hat{u}_B(t_1), \hat{u}_B(t_2), \ldots, u_B(t_n)$ are the corresponding glucose estimates.

Performance Analysis

Comprehensive Analysis

Figure 6:
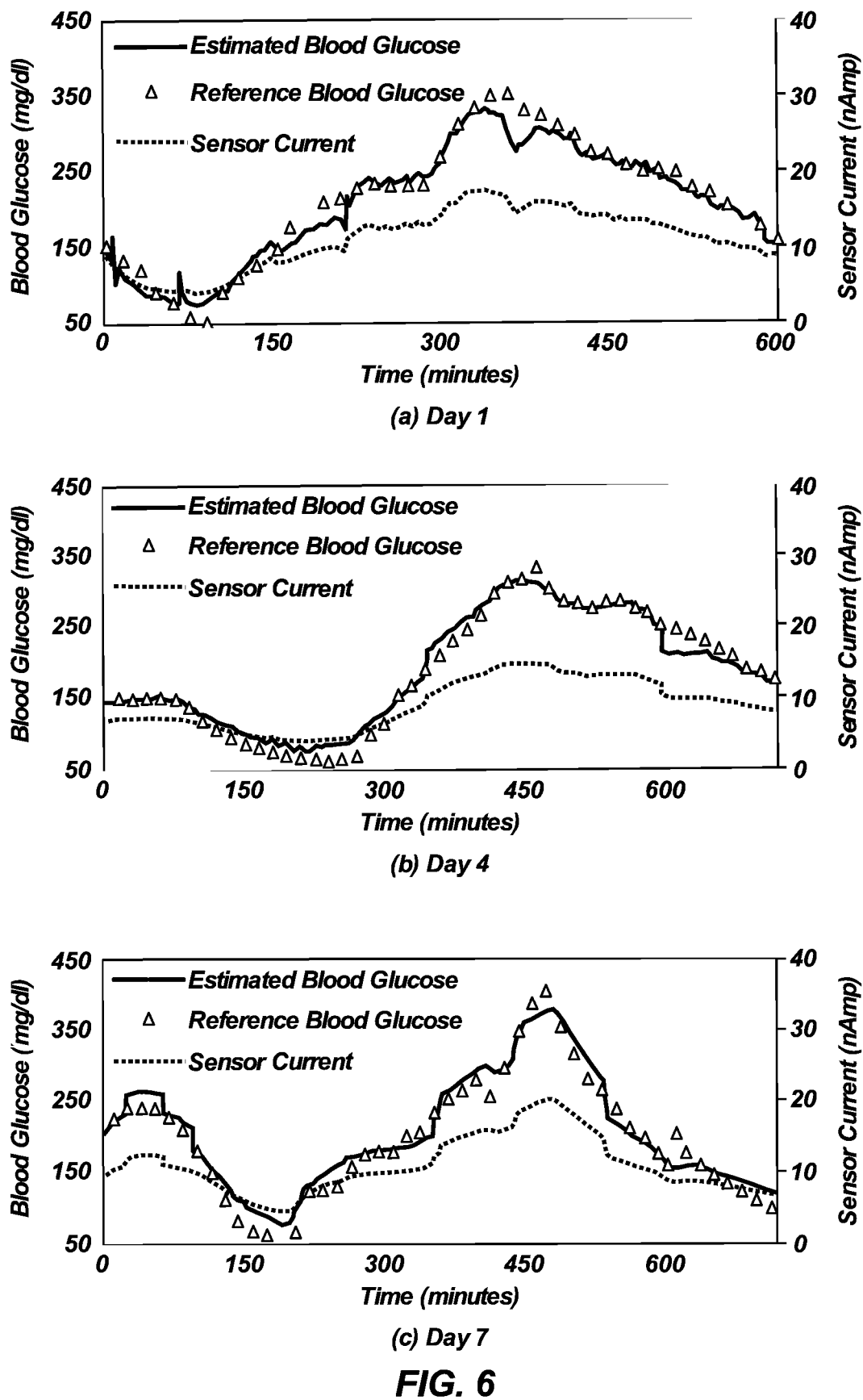
FIG. 6 is a set of graphs showing estimated blood glucose, reference glucose measurements, and sensor electric current in a sample patient on days 1, 4, and 7 of sensor wear time, the estimated blood glucose obtained via the methodology of FIG. 2.

A sample plot of estimated blood glucose, reference glucose measurements, and sensor electric current of a representative sensor datasets on days 1 (top graph), 4 (middle graph), and 7 (bottom graph) of the sensor age is shown in FIG. 6. The estimated glucose levels closely match the reference glucose measurements. Note the variation in sensor sensitivity between days (the sensor currents on days 1, 4, and 7 are different for similar ranges of measured glucose concentration), and that did not affect the accuracy of the disclosed method, supporting its ability in handling day-to-day variations in sensor sensitivity.

Figure 7:
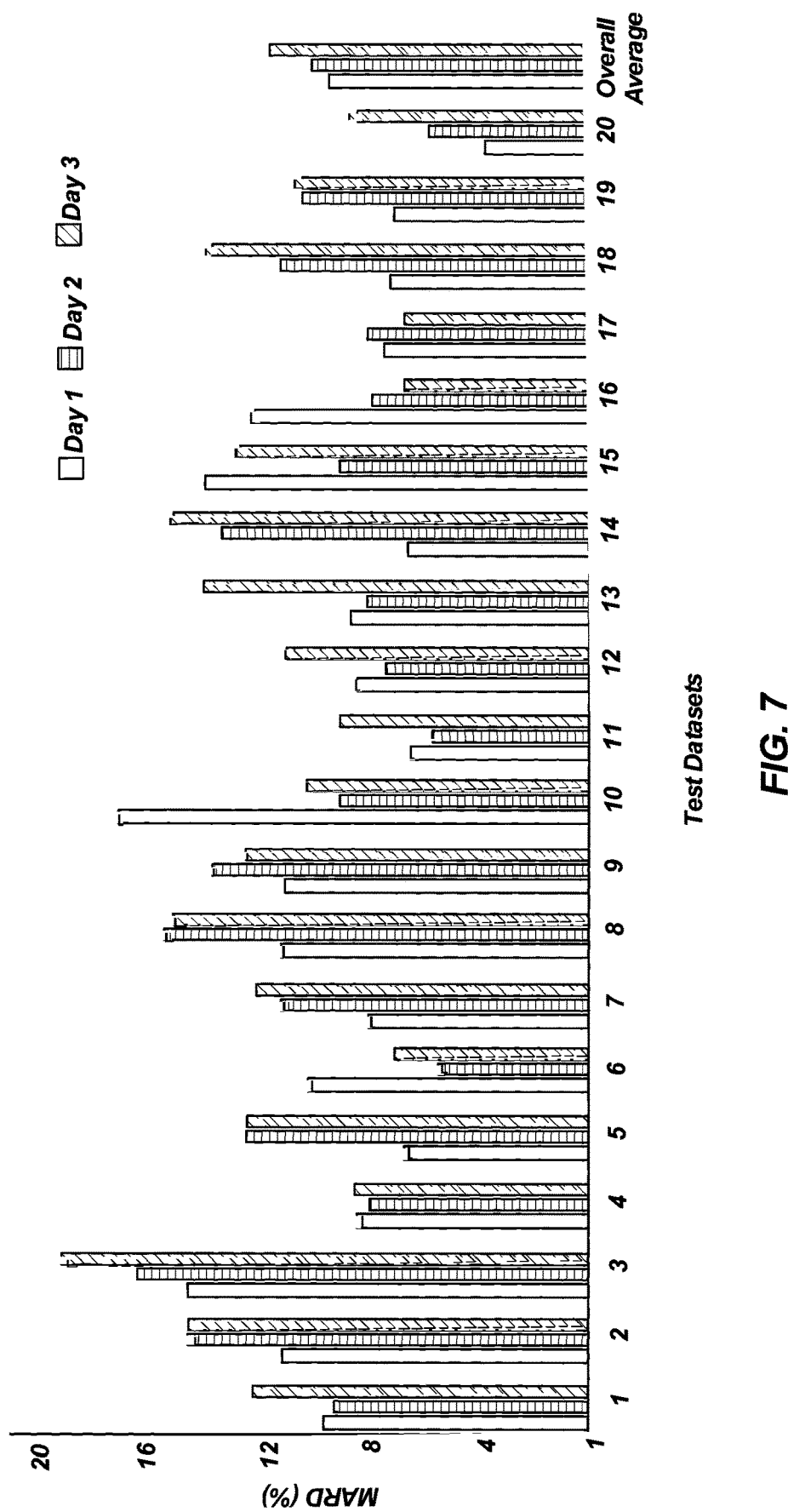
FIG. 7 is a graph showing Mean Absolute Relative Difference (MARD) of 20 sensor datasets on different days of sensor age.

The MARD of 20 sensor datasets on different days of sensor age is presented in FIG. 7, demonstrating that the disclosed method performs satisfactorily across different datasets and different sensor ages. Average MARD on days 1, 4, and 7 were 10.32%, 10.71%, and 11.89%, with an overall average of 10.97% (Table I).

TABLE I

Mean MARD of the proposed and alternative algorithms for 20 datasets

|  | Proposed algorithm | Alternative algorithm |
| --- | --- | --- |
| Day 1 | 10.32 | 12.46 |
| Day 4 | 10.71 | 15.75 |
| Day 7 | 11.89 | 14.17 |
| Overall average | 10.97 | 14.13 |

Comparison with an Alternative Method

The performance of the disclosed method was compared with an alternative method that uses minimum error variance estimator (instead of a Kalman filter) to estimate the calibration parameters. The average MARDs for this alternative method on days 1, 4, and 7 of sensor age were 12.46%, 15.75%, and 14.17%, and were larger than those of the disclosed method (Table I). Moreover, MARD higher than 25% was observed on 5 occasions with the alternative method compared to 0 occasion with the disclosed method.

Unlike the Kalman filter, the minimum error variance estimator does not update nor propagate, in real time, the prior information about the calibration parameters. This estimator requires instead separate priors with every parameters update (i.e., at calibration times). Reference glucose values on days 1, 4, and 7 in the training set are used to generate day-specific population priors, and priors for the days in between were obtained from the previous day with training data (i.e., prior for days 2 and 3 were estimated using datasets in day 1). This may have contributed to the degraded performance of the minimum error variance estimator.

Delay Analysis

Figure 8:
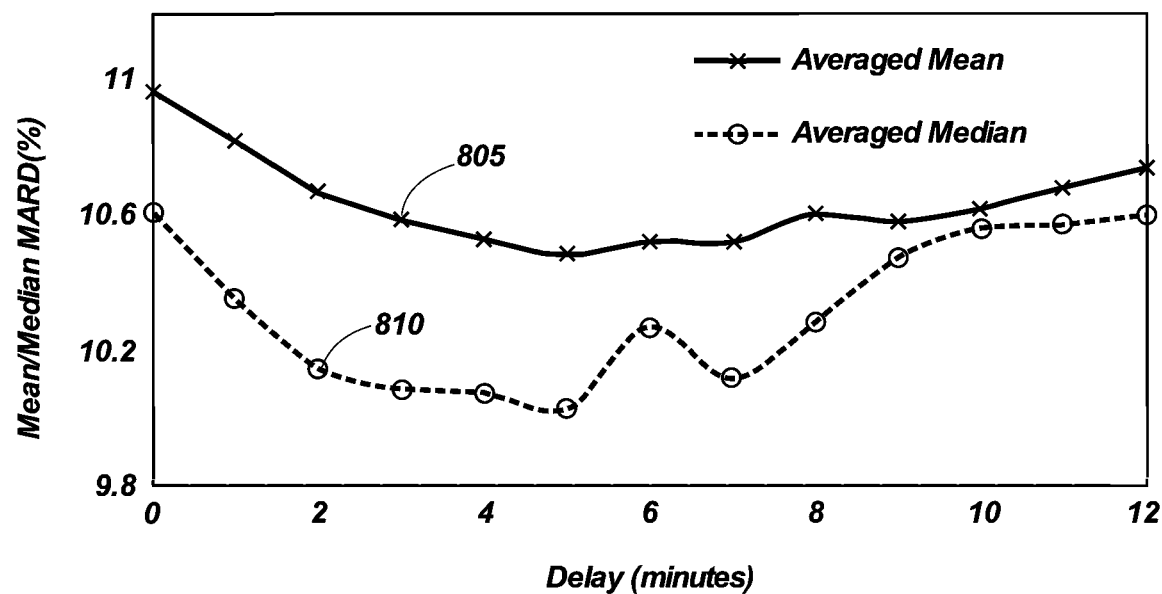
FIG. 8 is a graph showing Mean and Median MARDs when the reference glucose levels are shifted in time with various delay.

The disclosed method implements several Kalman filters, and each implementation introduces delay in the glucose estimation. Moreover, the glucose diffusion between the interstitial and the blood spaces introduces delay. The overall delay by plotting the mean and median MARDs were examined comparing the estimated glucose levels with shifted reference glucose levels by various values (FIG. 8). The mean and median MARDs achieve minimum values at 5-min shift, which indicates that the estimates lag the true glucose levels by around 5 minutes.

Estimation Accuracy of $\tau$

The Cubature Kalman filter estimated $\tau$ to be 5.4 min, using offline analysis of the training datasets. To assess this estimate, MARD was calculated for various $\tau$ values (Table II; remember that the testing datasets were not used to estimate $\tau$). The MARD was smallest at $\tau=5.4$, demonstrating the accuracy of the Cubature Kalman filter. Table II further shows a sharp decline in the glucose estimation accuracy with small deviation in $\tau$, demonstrating the importance of accurate offline analysis to estimate $\tau$.

TABLE II

MARD for various $\tau$

| | Average MARD | | | |
|---|---|---|---|---|
| $\tau$ | Day 1 | Day 4 | Day 7 | Overall mean |
| 4.8 | 11.76 | 15.71 | 19.04 | 15.50 |
| 4.9 | 11.24 | 14.20 | 17.16 | 14.20 |
| 5.0 | 10.85 | 12.99 | 15.55 | 13.13 |
| 5.1 | 10.57 | 12.01 | 14.21 | 12.26 |
| 5.2 | 10.39 | 11.26 | 13.13 | 11.59 |
| 5.3 | 10.31 | 10.85 | 12.35 | 11.17 |
| 5.4 | 10.32 | 10.71 | 11.89 | 10.97 |
| 5.5 | 10.40 | 10.84 | 11.69 | 10.98 |
| 5.6 | 10.53 | 11.19 | 11.73 | 11.15 |
| 5.7 | 10.72 | 11.74 | 11.96 | 11.47 |
| 5.8 | 10.96 | 12.44 | 12.34 | 11.91 |
| 5.9 | 11.23 | 13.27 | 12.87 | 12.46 |

Drift in Sensor Sensitivity

Figure 9:
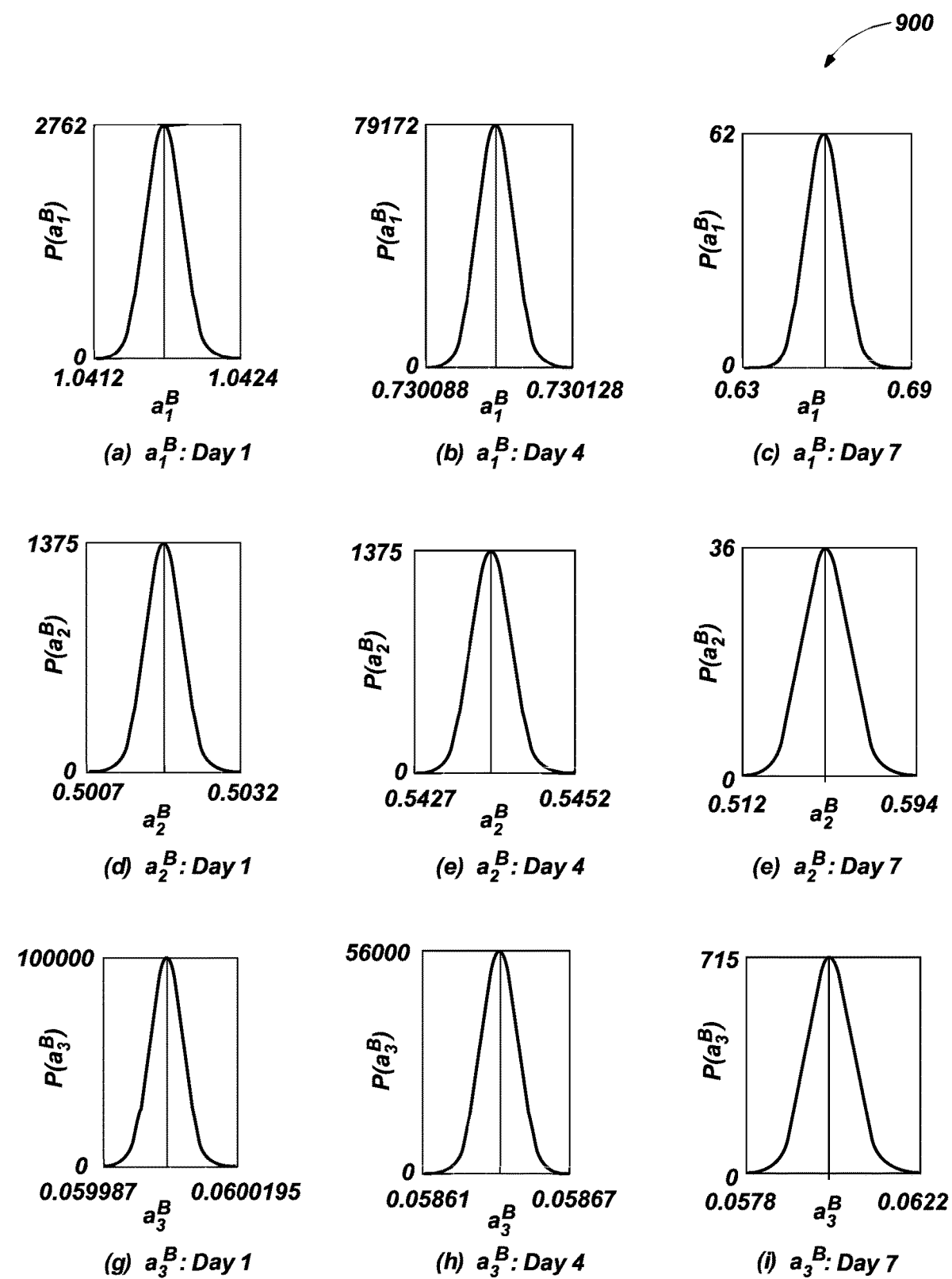
FIG. 9 is a set of graphs showing probability distributions of blood analyte calibration parameters $\{a_1^B, a_2^B \text{ and } a_3^B\}$ on different clinical days.

FIG. 9 shows the distribution of $a_1^B$, $a_2^B$, and $a_3^B$ in a sample subject over the sensor wear time. The calibration parameters change significantly between days, demonstrating the ability of the disclosed method to handle significant changes in sensor sensitivity. This also shows the limitation of using priors on days 2 and 3 derived from offline data on day 1 (as needed when using a minimum variance estimator).

Brief Discussion on Cubature Kalman Filtering (CKF)

The CKF is a nonlinear extension of linear Kalman filter, known for high accuracy at significantly low computational cost compared to other nonlinear filters. It is implemented over nonlinear state space model, represented by process and measurement models, as $$x_{k+1}=\phi(x_k)+w_k \quad (25)$$

and $$y_{k+1}=\gamma(x_{k+1})+v_k, \quad (26)$$

where $x_k \in \Re^n$ in and $y_k \in \Re^d$ are state and measurement variables, $\phi: x_k \to x_{k+1}$ and $\gamma: x_k \to y_{k+1}$ are nonlinear functions, and $w_k$ and $v_k$ are zero mean Gaussian noises with covariances $Q_k$ and $R_k$, respectively.

The steps involved in the implementation of CKF are explained below.

Offline Computation

For an n-dimensional system, the sample point set (a), also known as cubature points, and corresponding weight set (W) are computed offline, as $$\xi = \sqrt{n}\,[I_n - I_n]; \quad W = \frac{1}{2n} \cdot 1_{2n} \quad (27)$$

where $I_n$ is unity matrix and $1_{2n}$ is a 2n-dimensional array with all elements being 1.

Initialization and Parameter Tuning

The implementation of CKF is bound to the knowledge of initial estimate and covariance of $x_k$ i.e. $\hat{X}_{0|0}$ and $P_{0|0}$. Moreover, the noise covariances, $Q_k$ and $R_k$, also need to be defined.

Online Implementation Steps

The CKF is implemented through the following steps:

Prediction

Calculate the square root of posterior error covariance matrix by performing Cholesky decomposition:

$$P_{k|k}=S_{k|k}(S_{k|k})^T \quad (28)$$

Transform the cubature points for the given mean and covariance:

$$\xi_{j,k|k}=\hat{x}_{k|k}+S_{k|k}\xi_j \quad (29)$$

Update the transformed cubature points by propagating it through the given process equation (or state equation):

$$\xi_{j,k+1|k}=\phi(\xi_{j,k|k}) \quad (30)$$

Compute the mean and covariance:

$$\hat{x}_{k+1|k}=\Sigma_j W_j \xi_{j,k+1|k} \quad (31)$$

$$P_{k+1|k}=\Sigma_j W_j(\xi_{j,k+1|k}-\hat{x}_{k+1|k})(\xi_{j,k+1|k}-\hat{x}_{k+1|k})^T+Q_k \quad (32)$$

Compute the square-root of prior covariance:

$$P_{k+1|k}=S_{k+1|k}(S_{k+1|k})^T \quad (33)$$

Evaluate the transformed cubature points with the given mean and covariance:

$$\xi'_{j,k+1|k}=\hat{x}_{k+1|k}+S_{k+1|k}\xi_j \quad (34)$$

Propagate the transformed cubature points through given measurement equation:

$$Y_{j,k+1|k}=\gamma(\xi_{j,k+1|k}) \quad (35)$$

Estimate the mean of the predicted measurements:

$$\hat{y}_{k+1}=\Sigma_j W_j Y_{j,k+1|k} \quad (36)$$

Calculate the innovation covariance:

$$P_{yk+1,yk+1}=\Sigma_j W_j(Y_{j,k+1|k}-\hat{y}_{k+1})(Y_{j,k+1|k}-\hat{y}_{k+1})^T+R_k \quad (37)$$

Calculate the cross-covariance:

$$P_{xk+1,yk+1}=\Sigma_j W_j(\xi_{j,k+1|k}-\hat{x}_{k+1|k})(Y_{j,k+1|k}-\hat{y}_{k+1})^T \quad (38)$$

Calculate the Kalman gain:

$$K_{k+1}=P_{xk+1,yk+1}(P_{yk+1,yk+1})^{-1} \quad (39)$$

Compute the posterior mean:

$$\hat{x}_{k+1|k+1}=\hat{x}_{k+1|k}+K_{k+1}(y_{k+1}-\hat{y}_{k+1}) \quad (40)$$

Compute the posterior covariance:

$$P_{k+1|k+1}=+_{+1|k}-K_{k+1}P_{yk+1,yk+1}(K_{k+1})^T \quad (41)$$

Thus, disclosed herein is a Kalman-based calibration method for real-time continuous glucose monitoring systems. The disclosed method uses a (i) sequential Kalman filter to deconvolute interstitial sensor electrical current, (ii)

an ordinary, or in other words a conventional Kalman filter or a linear Kalman filter Kalman filter to estimate, in real time, sensor calibration parameters from intermittent capillary glucose measurements, and (iii) a cubature Kalman filter to estimate initial calibration parameters from offline training data. At calibration times, the method uses, as priors, patient-specific calibration parameters obtained from previous days data, as opposed to using population-level day-specific historical data. Improved performance compared to an alternative method based on minimum error variance estimator supports that using patient specific priors from previous days is advantageous over using population-level day-specific priors from historical data. Finally, the methodology disclosed herein benefits from a computational advantage as it avoids the need to implement a regularization-based direct deconvolution to match interstitial compartment to plasma compartment.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method of estimating an amount of glucose in blood of a subject, the method comprising:
   intermittently receiving, from a glucose sensor placed in interstitial fluid of the subject, current readings $y_I^{Tr}(t_i)$ at a first frequency at times $t_i$ reflective of an interstitial level of the glucose;
   intermittently receiving capillary blood glucose measurements $u_B(t_s)$ at a second frequency at times $t_s$, the capillary blood glucose measurements comprising an initial measurement and a subsequent measurement, wherein the second frequency is less than the first frequency;
   after receiving the initial measurement of the capillary blood glucose measurements, noise filtering the current readings $y_I^{Tr}(t_i)$ to provide noise filtered current readings $y_I(t_i)$ and generating a glucose sensor model based on the noise filtered current readings $y_I(t_i)$ and the initial measurement of the capillary blood glucose measurements;
   after receiving the initial measurement of the capillary blood glucose measurements and before receiving the subsequent measurement of the capillary blood glucose measurements, using the glucose sensor model to estimate a concentration of the glucose in the interstitial fluid as $\hat{u}_I(t_i) = \{y_I(t_i) - \hat{a}_2^I - \hat{a}_3^I \cdot \Delta t\}/\hat{a}_1^I$, where $\Delta t$ is a time since an insertion of the glucose sensor, and $\hat{a}_1^I$, $\hat{a}_2^I$ and $\hat{a}_3^I$ are interstitial calibration parameters;
   after receiving the subsequent measurement of the capillary blood glucose measurements:
      updating the glucose sensor model by:
         deconvoluting the noise filtered current readings $y_I(t_i)$ to obtain a hypothetical glucose sensor current $y_B(t_s)$;
         based on the hypothetical glucose sensor current $y_B(t_s)$ and a prior set of blood calibration parameters, obtaining updated blood calibration parameters; and
         updating the interstitial calibration parameters $\hat{a}_1^I$, $\hat{a}_2^I$ and $\hat{a}_3^I$ based on the updated blood calibration parameters; and
      using the updated glucose sensor model to estimate the concentration of the glucose; and
   sending one or more instructions to an insulin delivery system to deliver an amount of insulin based on the estimated concentration of the glucose.

2. The method of claim 1, wherein:
   deconvoluting the noise filtered current readings $y_I(t_i)$ comprises deconvoluting the noise filtered current readings $y_I(t_i)$ over $h(t) = \tau^{-1} e^{-t/\tau}$; and
   $\tau$ is a time constant of glucose diffusion from the blood to the interstitial fluid.

3. The method of claim 1, wherein:
   the updated blood calibration parameters comprise $\hat{a}_1^B(t_s)$, $\hat{a}_2^B(t_s)$ and $\hat{a}_3^B(t_s)$; and
   the interstitial calibration parameters $\hat{a}_1^I$, $\hat{a}_2^I$ and $\hat{a}_3^I$ are updated according to $\hat{a}_1^I = \hat{a}_1^B$, $\hat{a}_2^I = \hat{a}_2^B - \hat{a}_3^B \cdot \tau$, and $\hat{a}_3^I = \hat{a}B_3$, wherein $\tau$ is a time constant of glucose diffusion from the blood to the interstitial fluid.

4. The method of claim 1, wherein:
   the updated blood calibration parameters comprise $\hat{a}_1^B(t_s)$, $\hat{a}_2^B(t_s)$ and $\hat{a}_3^B(t_s)$; and
   the prior set of blood calibration parameters comprise $\hat{a}_1^B(t_s-1)$, $\hat{a}_2^B(t_s-1)$ and $\hat{a}_3^B(t_s-1)$.

5. The method of claim 1, wherein:
   the updated blood calibration parameters are estimated using a Kalman filter with a state defined as $X_S^{BCP} = [a_1^B, a_2^B, a_3^B]^T$.

6. The method of claim 5, wherein:
   state dynamics of the Kalman filter are characterized by a random walk model as $X_S^{BCP} = X_{S-1}^{BCP} + w_{S-1}^{BCP}$ where $w_{S-1}^{BCP}$ is zero mean Gaussian noise added to compensate for possible changes in blood calibration parameters between calibration points.

7. The method of claim 1, wherein noise filtering the current readings comprises heuristically filtering out a low frequency high magnitude noise component and filtering out a high frequency low magnitude component via Kalman filtering.

8. The method of claim 7, wherein heuristic filtering out the low frequency high magnitude noise component comprises using a mean of previous measurements of the current readings over a predetermined time period as a current reading of the current readings $y_I^{Tr}(t_i)$.

9. The method of claim 7, wherein heuristic filtering out the low frequency high magnitude noise component comprises:
   determining that a measurement of the current readings in a respective measurement period is greater than twice a mean of an immediately prior measurement period; and
   in response to the determining, setting a mean of the measurement of the current readings in the respective measurement period as the mean of the immediately prior measurement period.

10. The method of claim 1, further comprising, when the initial measurement of the capillary blood glucose measurements is not available to calibrate the current readings, delaying the noise filtering of the current readings until the initial measurement of the capillary blood glucose measurements is available.

11. The method of claim 1, wherein the hypothetical glucose sensor current represents a glucose sensor current if the glucose sensor was inserted in the blood instead of the interstitial fluid.

12. The method of claim 1, wherein the updated blood calibration parameters comprise $a^B_1$, $a^B_2$ and $a^B_3$ and are obtained based on the subsequent measurement of the capillary blood glucose measurements, $u_B(t_S)$ according to: $y_B(t_s)=a^B_1 \cdot u_B(t_S)+a^B_2+a^B_3 \cdot \Delta t$.

13. The method of claim 1, wherein the deconvoluting the noise filtered current readings is via a sequential Kalman filter implemented over a time window in which the noise filtered current readings is sampled at a sampling interval to obtain samples, and for each sample, a recursion of the sequential Kalman filter is performed and the sequential Kalman filter adds a new state.

14. The method of claim 1, wherein the updated blood calibration parameters are obtained using a Kalman filter that uses the hypothetical glucose sensor current as a measurement variable.

15. A non-transitory computer-readable storage medium with instructions stored thereon for calibrating a glucose sensor placed in interstitial fluid of a subject, wherein a processor is configured to execute the instructions to perform operations comprising:
  intermittently receiving, from the glucose sensor, current readings $y_I^{Tr}(t_i)$ at a first frequency at times $t_i$ reflective of an interstitial level of glucose;
  intermittently receiving capillary blood glucose measurements $u_B(t_s)$ at a second frequency at times $t_s$, the capillary blood glucose measurements comprising an initial measurement and a subsequent measurement, wherein the second frequency is less than the first frequency;
  after receiving the initial measurement of the capillary blood glucose measurements, noise filtering the current readings to provide noise filtered current readings $y_f(t_i)$ and generating a glucose sensor model based on the noise filtered current readings $y_f(t_i)$ and the initial measurement of the capillary blood glucose measurements;
  after receiving the initial measurement of the capillary blood glucose measurements and before receiving the subsequent measurement of the capillary blood glucose measurements, using the glucose sensor model to estimate a concentration of the glucose in the interstitial fluid as $\hat{u}_I(t_i)=\{y_f(t_i)-\hat{a}^I_2-\hat{a}^I_3 \cdot \Delta t\}/\hat{a}^I_1$, where $\Delta t$ is a time since an insertion of the glucose sensor, and $\hat{a}^I_1$, $\hat{a}^I_2$ and $\hat{a}^I_3$ are interstitial calibration parameters;
  after receiving the subsequent measurement of the capillary blood glucose measurements:
    updating the glucose sensor model by:
      deconvoluting the noise filtered current readings $y_f(t_i)$ to obtain a hypothetical glucose sensor current $y_B(t_s)$;
      based on the hypothetical glucose sensor current $y_B(t_s)$ and a prior set of blood calibration parameters, obtaining updated blood calibration parameters;
      updating the interstitial calibration parameters $\hat{a}^I_1$, $\hat{a}^I_2$ and $\hat{a}^I_3$ based on the updated blood calibration parameters; and
    using the updated glucose sensor model to estimate the concentration of the glucose; and
  sending one or more instructions to an insulin delivery system to deliver an amount of insulin based on the estimated concentration of the glucose.

16. The non-transitory computer-readable storage medium of claim 15, wherein:
  deconvoluting the noise filtered current readings $y_f(t_i)$ comprises deconvoluting the noise filtered current readings $y_f(t_i)$ over $h(t)=\tau^{-1}e^{-t/\tau}$; and
  $\tau$ is a time constant of glucose diffusion from blood of the subject to the interstitial fluid.

17. The non-transitory computer-readable storage medium of claim 15, wherein:
  the updated blood calibration parameters comprise $\hat{a}^B_1(t_s)$, $\hat{a}^B_2(t_s)$ and $\hat{a}^B_3(t_s)$; and
  the interstitial calibration parameters $\hat{a}^I_1$, $\hat{a}^I_2$ and $\hat{a}^I_3$ are updated according to $\hat{a}^I_1=\hat{a}^B_1$, $\hat{a}^I_2=\hat{a}^B_2-\hat{a}^B_3 \cdot \tau$, and $\hat{a}^I_3=\hat{a}B_3$, where $\tau$ is a time constant of glucose diffusion from blood of the subject to the interstitial fluid.

18. A system for estimating an amount of a glucose in a subject, comprising a glucose sensor and a processor in communication with the glucose sensor, wherein the processor is configured to perform operations comprising:
  receiving from the glucose sensor a current reading reflective of an interstitial level of the glucose in the subject;
  noise filtering the current reading to obtain a noise filtered current reading;
  deconvoluting the noise filtered current reading via a sequential Kalman filter to obtain a predicted blood glucose sensor current reading;
  estimating blood calibration parameters based on the predicted blood glucose sensor current reading via a Kalman filter that uses the predicted blood glucose sensor current reading as a measurement variable, wherein estimating the blood calibration parameters comprises initializing the Kalman filter based on an initial blood glucose calibration parameter state estimate and an initial blood glucose calibration parameter covariance;
  updating interstitial calibration parameters based on the estimated blood calibration parameters;
  estimating a concentration of the glucose based on the updated interstitial calibration parameters; and
  sending one or more instructions to an insulin delivery system to deliver an amount of insulin based on the estimated concentration of the glucose.

19. The system of claim 18, wherein the operations comprise determining the initial blood glucose calibration parameter state estimate and the initial blood glucose calibration parameter covariance via the Kalman filter, wherein the Kalman filter is a cubature Kalman filter.

20. The system of claim 18, wherein the operations comprise arbitrarily assigning the initial blood glucose calibration parameter state estimate and the initial blood glucose calibration parameter covariance.

* * * * *